US012329506B2

(12) United States Patent
Shin et al.

(10) Patent No.: US 12,329,506 B2
(45) Date of Patent: Jun. 17, 2025

(54) SMART HOME DEVICE USING A SINGLE RADAR TRANSMISSION MODE FOR ACTIVITY RECOGNITION OF ACTIVE USERS AND VITAL SIGN MONITORING OF INACTIVE USERS

(71) Applicant: Google LLC, Mountain View, CA (US)

(72) Inventors: Dongeek Shin, Santa Clara, CA (US); Michael Dixon, Sunnyvale, CA (US); Andrew William Goldenson, Belmont, CA (US)

(73) Assignee: Google LLC, Mountain View, CA (US)

( * ) Notice: Subject to any disclaimer, the term of this patent is extended or adjusted under 35 U.S.C. 154(b) by 1 day.

(21) Appl. No.: 18/026,875

(22) PCT Filed: Sep. 21, 2020

(86) PCT No.: PCT/US2020/051776
§ 371 (c)(1),
(2) Date: Mar. 17, 2023

(87) PCT Pub. No.: WO2022/060369
PCT Pub. Date: Mar. 24, 2022

(65) Prior Publication Data
US 2023/0329574 A1 Oct. 19, 2023

(51) Int. Cl.
*A61B 5/0507* (2021.01)
*A61B 5/00* (2006.01)
(Continued)

(52) U.S. Cl.
CPC .......... *A61B 5/0507* (2013.01); *A61B 5/4809* (2013.01); *G01S 13/32* (2013.01);
(Continued)

(58) Field of Classification Search
CPC ... A61B 5/0507; A61B 5/4809; A61B 5/1115; A61B 5/7207; A61B 5/7264;
(Continued)

(56) References Cited

U.S. PATENT DOCUMENTS 10,417,923 B2    9/2019 Walter et al.
10,754,002 B1 *  8/2020 Gibbons ................. G01S 3/801
(Continued)

FOREIGN PATENT DOCUMENTS

CN    108700645 A    10/2018
CN    109303556 A    2/2019
(Continued)

OTHER PUBLICATIONS

International Search Report and Written Opinion for PCT/US2020/051776 mailed Jun. 18, 2021, all pages.

*Primary Examiner* — Adil Partap S Virk
(74) *Attorney, Agent, or Firm* — Kilpatrick Townsend & Stockton LLP

(57) ABSTRACT

Various arrangements for monitoring for contactless human interactions and health using a single radar transmission modulation mode are provided. Radar chirps may be output by a radar sensor operating in a burst mode. The burst mode radar data stream may be monitored for a contactless human interaction performed by an active user. The burst mode radar data stream may be converted to a virtual continuous mode radar data stream. Health monitoring of an inactive user may be performed using the virtual continuous mode radar data stream.

20 Claims, 10 Drawing Sheets

(51) Int. Cl.
  *G01S 13/32* (2006.01)
  *G01S 13/88* (2006.01)
  *G06F 3/01* (2006.01)
  *G06F 3/16* (2006.01)

(52) U.S. Cl.
  CPC .............. *G01S 13/88* (2013.01); *G06F 3/017* (2013.01); *G06F 3/167* (2013.01)

(58) Field of Classification Search
  CPC ........ G01S 13/32; G01S 13/88; G01S 13/343; G06F 3/017; G06F 3/167
  See application file for complete search history.

(56) References Cited

U.S. PATENT DOCUMENTS

| | | | |
|---|---|---|---|
| 2007/0106183 A1* | 5/2007 | Suzuki | A61B 5/4812 600/595 |
| 2015/0219755 A1 | 8/2015 | Borggaard et al. | |
| 2015/0260828 A1* | 9/2015 | Ossowska | G01S 13/931 342/162 |
| 2017/0219689 A1* | 8/2017 | Hung | G01S 7/0232 |
| 2018/0156907 A1* | 6/2018 | Cegla | G01S 15/105 |
| 2019/0041495 A1* | 2/2019 | Steinbuch | G01S 7/40 |
| 2019/0044485 A1* | 2/2019 | Rao | G01S 13/931 |
| 2019/0212428 A1* | 7/2019 | Santra | G01S 7/4865 |
| 2019/0391249 A1 | 12/2019 | Takeuchi et al. | |
| 2020/0234030 A1 | 7/2020 | Baheti et al. | |
| 2020/0284901 A1 | 9/2020 | Tierney et al. | |

FOREIGN PATENT DOCUMENTS

| | | |
|---|---|---|
| CN | 111190183 A | 5/2020 |
| DE | 102018105875 A1 | 9/2019 |
| DE | 102018210083 A1 | 12/2019 |
| JP | 2016135194 A | 7/2016 |
| JP | 2017181225 A | 10/2017 |
| JP | 2019023595 A | 2/2019 |
| JP | 2020024185 A | 2/2020 |
| JP | 2020056629 A | 4/2020 |
| WO | 2018220701 A1 | 12/2018 |
| WO | 2019005936 A1 | 1/2019 |
| WO | 2019/122413 A1 | 6/2019 |
| WO | 2019226956 A1 | 11/2019 |
| WO | 2020049648 A1 | 3/2020 |

* cited by examiner

SMART HOME DEVICE USING A SINGLE RADAR TRANSMISSION MODE FOR ACTIVITY RECOGNITION OF ACTIVE USERS AND VITAL SIGN MONITORING OF INACTIVE USERS

CROSS-REFERENCES TO RELATED APPLICATIONS

This application is a 371 National Stage filing of PCT Application No. PCT/US2020/051776, filed Sep. 21, 2020, the entire disclosure of this application is hereby incorporated by reference for all purposes. This application is related to the following applications: PCT Application PCT/US2019/031290, filed May 8, 2019, entitled "Sleep Tracking and Vital Sign Monitoring Using Low Power Radio Waves;" U.S. patent application Ser. No. 16/990,714, filed Aug. 11, 2020, entitled "Contactless Sleep Detection and Disturbance Attribution for Multiple Users;" U.S. patent application Ser. No. 16/990,705, filed Aug. 11, 2020, entitled "Contactless Sleep Detection and Disturbance Attribution; U.S. patent application Ser. No. 16/990,720, filed Aug. 11, 2020, entitled "Contactless Cough Detection and Attribution; US Pat. App. No. 16/990,726, filed Aug. 11, 2020, entitled "Precision Sleep Tracking Using a Contactless Sleep Tracking Device;" U.S. patent application Ser. No. 16/990,746, filed Aug. 11, 2020, entitled "Initializing Sleep Tracking on a Contactless Health Tracking Device;" and PCT Application PCT/US2020/048388, filed Aug. 28, 2020, entitled "Precision Sleep Tracking Using a Contactless Sleep Tracking Device." The entire disclosures of these applications are hereby incorporated by reference for all purposes.

BACKGROUND

It can be convenient for a user to interact with a device without making any physical contact with the device (or another input device). For instance, hand gestures may be performed and detected by a device and interpreted as a command. While such contactless interactions are useful, the ability of the device to perform other tasks without contact may also be desired. Such other tasks may have competing requirements that need to be balanced with detection of contactless interactions.

SUMMARY

Various embodiments are described related to a contactless health monitoring device. In some embodiments, a contactless health monitoring device is described. The device may comprise a housing. The device may comprise a radar sensor, housed by the housing, configured to operate in a burst mode in which the radar sensor emits a plurality of bursts of radar chirps. A first amount of time elapsing between multiple radar chirps of a burst of the plurality of bursts of radar chirps may be smaller than a second amount of time elapsing between subsequent bursts of the plurality of bursts of radar chirps. The radar sensor outputs a burst mode radar data stream that may be based on reflections of the radar chirps of the plurality of bursts or radar chirps. The device may comprise a processing system, housed by the housing, comprising one or more processors, that may be in communication with the radar sensor. The processing system may be configured to receive the burst mode radar data stream from the radar sensor. The processing system may be configured to analyze the burst mode radar data stream to identify a contactless human interaction. The processing system may be configured to convert the burst mode radar data stream to a virtual continuous mode radar data stream. The processing system may be configured to perform health monitoring of a user using the virtual continuous mode radar data stream.

Embodiments of such a device may include one or more of the following features: the virtual continuous mode radar data stream may be comprised of a plurality of virtual reflections of radar chirps spaced equally in time. The processing system being configured to convert the burst mode radar data stream to the virtual continuous mode radar data stream may comprise the processing system being configured to create a virtual reflection of a radar chirp based on the multiple radar chirps of a burst of the plurality of bursts. The virtual reflection of the radar chirp may be part of the plurality of virtual reflections of radar chirps spaced equally in time. The processing system being configured to create the virtual reflection of the radar chirp based on the multiple radar chirps of the burst of the plurality of bursts may comprise the processing system being configured to perform an averaging process. The processing system may comprise sampling a plurality of samples of each radar chirp of the multiple chirps of the burst. The processing system may comprise averaging each sample of the plurality of samples with corresponding samples from the other chirps of the multiple chirps of the burst to create a plurality of averaged samples. The processing system may comprise assembling the averaged samples to create the virtual reflection of the radar chirp. The contactless human interaction may be detected while health monitoring is being performed. The radar sensor may output frequency-modulated continuous wave (FMCW) radar. The contactless human interaction may be a gesture. The contactless human interaction may be presence detection. The health monitoring may comprise sleep monitoring of the user. The virtual continuous mode radar data stream may have higher resolution than the burst mode radar data stream due to dithering. The device may further comprise a wireless network interface housed by the housing. The device may further comprise an electronic display housed by the housing. The device may further comprise a microphone housed by the housing. The device may further comprise a speaker housed by the housing. The wireless network interface, the electronic display, the microphone, and the speaker may be in communication with the processing system. The processing system may be further configured to receive a spoken command via the microphone. The processing system may be further configured to transmit an indication of the spoken command via the wireless network interface to a cloud-based server system. The processing system may be further configured to receive a response from the cloud-based server system via the wireless network interface. The processing system may be further configured to output information obtained from the performed health monitoring via the electronic display, the speaker, or both based on the response from the cloud-based server system. The processing system may be further configured to output a report based on the health monitoring.

In some embodiments, a method for monitoring for contactless human interactions and monitoring health using a single radar modulation mode is described. The method may comprise emitting radar chirps, by a radar sensor operating in a burst mode, such that the radar sensor emits a plurality of bursts of radar chirps. A first amount of time elapsing between subsequent radar chirps of a burst of the plurality of bursts of radar chirps may be smaller than a second amount of time elapsing between subsequent bursts of the plurality of bursts of radar chirps. The radar sensor outputs a burst mode radar data stream that may be based on reflections of the radar chirps of the plurality of bursts or radar chirps. The method may comprise receiving, by a processing system, the burst mode radar data stream from the radar sensor. The method may comprise analyzing, by the processing system, the burst mode radar data stream for a contactless human interaction. The method may comprise converting, by the processing system, the burst mode radar data stream to a virtual continuous mode radar data stream. The method may comprise performing, by the processing system, health monitoring of a user using the virtual continuous mode radar data stream.

Embodiments of such a method may include one or more of the following features: the virtual continuous mode radar data stream may be comprised of a plurality of virtual reflections of radar chirps spaced equally in time. The processing system being configured to convert the burst mode radar data stream to the virtual continuous mode radar data stream may comprise the processing system being configured to create a virtual reflection of a radar chirp based on the multiple radar chirps of a burst of the plurality of bursts. The virtual reflection of the radar chirp may be part of the plurality of virtual reflections of radar chirps spaced equally in time. Creating the virtual reflection of the radar chirp based on the multiple radar chirps of the burst of the plurality of bursts may comprise sampling a plurality of samples of each radar chirp of the multiple chirps of the burst. Creating the virtual reflection of the radar chirp based on the multiple radar chirps of the burst of the plurality of bursts may comprise averaging each sample of the plurality of samples with corresponding samples from the other chirps of the multiple chirps of the burst to create a plurality of averaged samples. Creating the virtual reflection of the radar chirp based on the multiple radar chirps of the burst of the plurality of bursts may comprise assembling the averaged samples to create the virtual reflection of the radar chirp. The contactless human interaction may be a gesture. The contactless human interaction may be presence detection. The health monitoring may comprise sleep monitoring of the user.

Various arrangements of smart home devices are present in some embodiments. A smart home device can include a housing that is configured for placement of the smart home device in areas of user activity, user sleep, or both. A smart home device can include a radar sensor, housed by the housing, configured to operate in a burst mode in which the radar sensor transmits a plurality of bursts of radar chirps, receives reflections of the plurality of bursts of radar chirps, and outputs a single radar data stream based on the reflections of the plurality of bursts of radar chirps. A first amount of time can elapse between adjacent radar chirps of a burst of the plurality of bursts of radar chirps is smaller than a second amount of time elapsing between adjacent bursts of the plurality of bursts of radar chirps. A smart home device can include a processing system, housed by the housing, comprising one or more processors, that is in communication with the radar sensor. The processing system can be configured to perform a first set of operations on the single radar data stream to perform user activity recognition. The processing system can be configured to perform a second set of operations on the single radar data stream to perform user vital sign detection, wherein no radar transmission mode changes are required to perform both the user activity recognition and the user vital sign detection using the single radar data stream.

Embodiments of such smart home devices can include one or more of the following features: The second set of operations can include instructions to convert the single radar data stream to a virtual continuous mode radar data stream. The user activity recognition can be gesture detection. The virtual continuous mode radar data stream can include a plurality of virtual reflections of radar chirps spaced equally in time. The instructions to convert the single radar data stream to the virtual continuous mode radar data stream can include instructions that cause the processing system to create a virtual reflection of a radar chirp based on the multiple radar chirps of a burst of the plurality of bursts, wherein the virtual reflection of the radar chirp is part of the plurality of virtual reflections of radar chirps spaced equally in time.

The processing system being configured to create the virtual reflection of the radar chirp based on the multiple radar chirps of the burst of the plurality of bursts can include the processing system being configured to perform an averaging process, comprising: sampling a plurality of samples of each radar chirp of the multiple chirps of the burst; averaging each sample of the plurality of samples with corresponding samples from the other chirps of the multiple chirps of the burst to create a plurality of averaged samples; and assembling the averaged samples to create the virtual reflection of the radar chirp. The user activity recognition can be performed while detection of the user vital sign is being performed. The radar sensor can output frequency-modulated continuous wave (FMCW) radar having a frequency between 57-64 GHz and a peak EIRP of less than 20 dBm.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Embodiments detailed herein are focused on a device performing contactless health monitoring, such as contactless sleep monitoring, while also monitoring for contactless human interactions. Contactless health monitoring can involve tracking a user's sleep (of an inactive user), monitoring a user's vital signs, tracking a user's coughs, etc. Contactless health monitoring may be performed using radar. A contactless human interaction can be a gesture (e.g., a user moving his hand or arm in a particular way that is to be interpreted as a command) or presence (e.g., a user being detected as present within a vicinity of the device) as performed by an active user. A device may monitor for contactless human interactions using radar.

Since both contactless health monitoring and contactless human interaction monitoring can use radar, competing demands can be present between the two types of monitoring. For example, contactless health monitoring may be performed effectively when the radar sensor is operated in a continuous mode. In a continuous mode, a radar chirp may be received periodically. However, for human interaction monitoring to be performed effectively, the radar sensor may be operated in a burst mode. In burst mode, a series of radar chirps (a "burst") are emitted, then a period of time is waited before starting a next burst of radar chirps. The period of time waited between bursts may be to limit the total amount of energy emitted into an environment of the user, thereby decreasing the user's exposure to RF energy.

In embodiments detailed herein, a radar sensor may be operated in burst mode. Therefore, the radar data stream output by the radar sensor may be optimized for human interaction monitoring. Processing may be performed on the radar data stream to create a virtual continuous mode radar data stream. This virtual continuous mode radar data stream can be created such that the virtual continuous mode radar data stream comprises higher-quality data than if the radar sensor itself operated in continuous mode.

By creating a virtual continuous mode radar data stream, a single device or system that receives the radar data stream can effectively monitor for human interactions in burst mode and perform health monitoring in a continuous mode. Therefore, a single device may be able to effectively respond to a contactless human interaction while health monitoring is being performed without a user having to switch a mode of the device or system. Similarly, the device or system can continuously operate the radar sensor in burst mode without having to change the mode in which the radar sensor operates. Rather, the device or system continuously creates a virtual continuous mode radar data stream, thereby allowing monitoring for contactless user interactions and contactless health monitoring to occur simultaneously and independent of each other.

Figure 1:
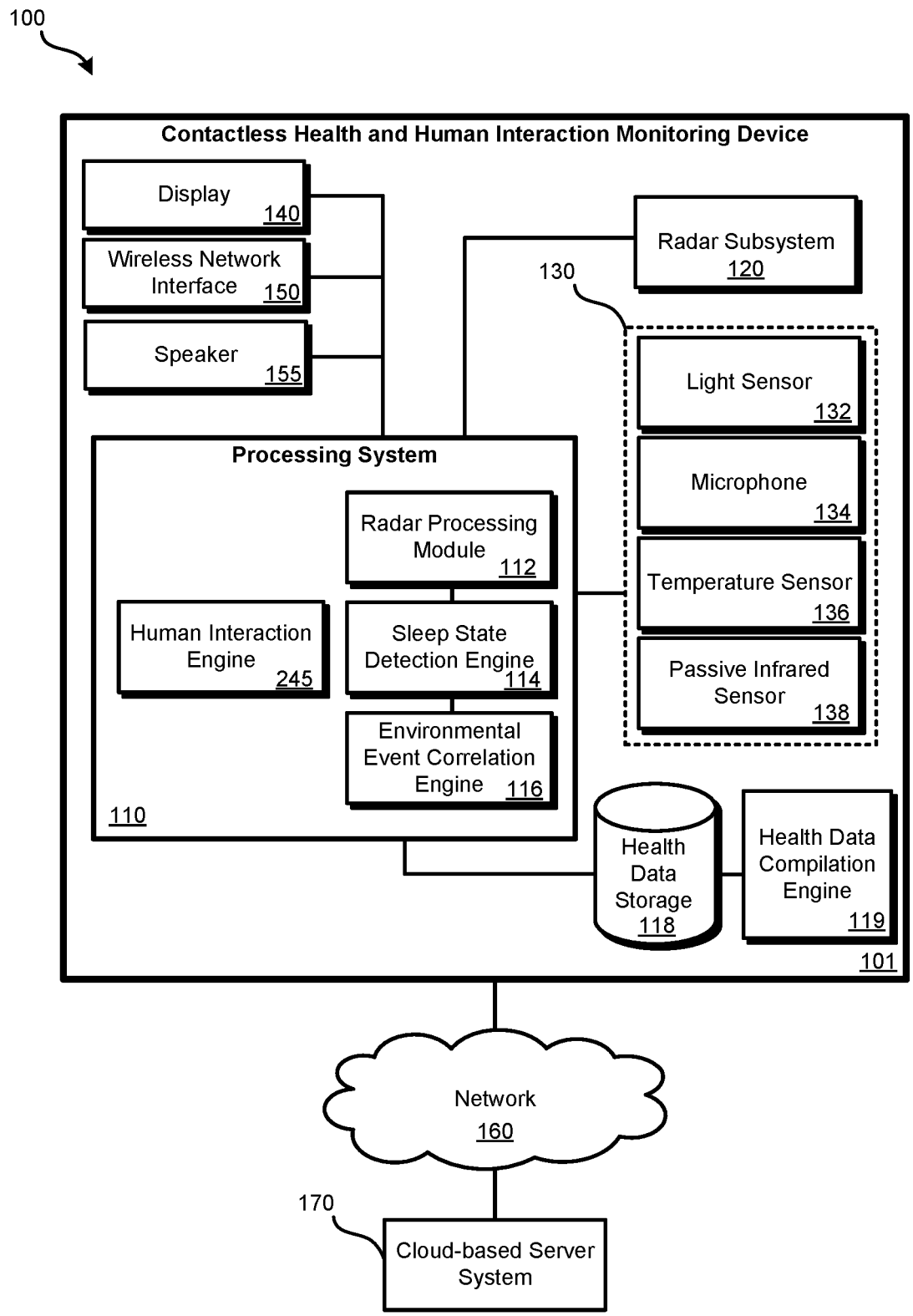
FIG. 1 illustrates an embodiment of a system for performing contactless health and user interaction monitoring.

Further detail regarding such embodiments and additional embodiments can be understood in relation to the figures. FIG. 1 illustrates an embodiment of a system 100 for performing contactless health and user interaction monitoring. System 100 can include: contactless health and human interaction monitoring device 101 ("device 101"); network 160; and cloud-based server system 170. Device 101 can include: processing system 110; sleep data storage 118; radar subsystem 120; environmental sensor suite 130; electronic display 140; wireless network interface 150; and speaker 155. Generally, device 101 can include a housing that houses all of the components of device 101. Further detail regarding such a possible housing is provided in relation to FIG. 3A and FIG. 3B. Device 101 can also be referred to as a health monitoring device, a health tracking device, a sleep monitoring device, a sleep tracking device, or a home assistant device.

Processing system 110 can include one or more processors configured to perform various functions, such as the functions of: radar processing module 112; sleep state detection engine 114; and environmental event correlation engine 116. Processing system 110 can include one or more special-purpose or general-purpose processors. Such special-purpose processors may include processors that are specifically designed to perform the functions detailed herein. Such special-purpose processors may be ASICs or FPGAs which are general-purpose components that are physically and electrically configured to perform the functions detailed herein. Such general-purpose processors may execute special-purpose software that is stored using one or more non-transitory processor-readable mediums, such as random access memory (RAM), flash memory, a hard disk drive (HDD), or a solid state drive (SSD).

Radar subsystem 120 (also referred to as a radar sensor), can be a single integrated circuit (IC) that emits, receives, and outputs a radar data stream indicative of received reflected radio waves. The output of radar subsystem 120 may be analyzed using radar processing module 112 of processing system 110. Further detail regarding radar subsystem 120 and radar processing module 112 is provided in relation to FIG. 2.

Device 101 may include one or more environmental sensors, such as all, one, or some combination of the environmental sensors provided as part of environmental sensor suite 130. Environmental sensor suite 130 can include: light sensor 132; microphone 134; temperature sensor 136; and passive infrared (PIR) sensor 138. In some embodiments, multiple instances of some or all of these sensors may be present. For instance, in some embodiments, multiple microphones may be present. Light sensor 132 may be used for measuring an ambient amount of light present in the general environment of device 101. Microphone 134 may be used for measuring an ambient noise level present in the general environment of device 101. Temperature sensor 136 may be used for measuring an ambient temperature of the general environment of device 101. PIR 138 may be used to detect moving living objects (e.g., persons, pets) within the general environment of device 101. Other types of environmental sensors are possible. For instance, a camera and/or humidity sensor may be incorporated as part of environmental sensor suite 130. In some embodiments, some data, such as humidity data, may be obtained from a nearby weather station that has data available via the Internet.

Device 101 may include various interfaces. Display 140 can allow processing system 110 to present information for viewing by one or more users. Wireless network interface 150 can allow for communication using a wireless local area network (WLAN), such as a WiFi-based network. Speaker 155 can allow for sound, such as synthesized speech, to be output. For instance, responses to spoken commands received via microphone 134 may be output via speaker 155 and/or display 140. The spoken commands may be analyzed locally by device 101 or may be transmitted via wireless network interface 150 to cloud-based server system 170 for analysis. A response, based on the analysis of the spoken command, can be sent back to device 101 via wireless network interface 150 for output via speaker 155 and/or display 140. Additionally or alternatively, the speaker 155 and microphone 134 may be collectively configured for active acoustic sensing, including ultrasonic acoustic sensing. Additionally or alternatively, other forms of wireless communication may be possible, such as using a low-power wireless mesh network radio and protocol (e.g., Thread) to communicate with various smart home devices. In some embodiments, a wired network interface, such as an Ethernet connection, may be used for communication with a network. Further, the evolution of wireless communication to fifth generation (5G) and sixth generation (6G) standards and technologies provides greater throughput with lower latency which enhances mobile broadband services. 5G and 6G technologies also provide new classes of services, over control and data channels, for vehicular networking (V2X), fixed wireless broadband, and the Internet of Things (IoT). Such standards and technologies may be used for communication by device 101.

The low-power wireless mesh network radio and protocol may be used for communicating with power limited devices. A power-limited device may be an exclusively battery powered device. Such devices may rely exclusively on one or more batteries for power and therefore, the amount of power used for communications may be kept low in order to decrease the frequency at which the one or more batteries need to be replaced. In some embodiments, a power-limited device may have the ability to communicate via a relatively high power network (e.g., WiFi) and the low-power mesh network. The power-limited device may infrequently use the relatively high power network to conserve power. Examples of such power-limited devices include environmental sensors (e.g., temperature sensors, carbon monoxide sensors, smoke sensors, motion sensors, presence detectors) and other forms of remote sensors.

Wireless network interface 150 can allow for wireless communication with network 160. Network 160 can include one or more public and/or private networks. Network 160 can include a local wired or wireless network that is private, such as a home WLAN. Network 160 may also include a public network, such as the Internet. Network 160 can allow for device 101 to communicate with remotely-located cloud-based server system 170.

Cloud-based server system 170 can provide device 101 with various services. Regarding sleep data, cloud-based server system 170 can include processing and storage services for sleep-related data. While the embodiment of FIG. 1 involves processing system 110 performing sleep state detection and environmental event correlation, in other embodiments, such functions may be performed by cloud-based server system 170. Also, in addition or in alternate to sleep data storage 118 being used to store sleep data, sleep-related data may be stored by cloud-based server system 170, such as mapped to a common user account to which device 101 is linked. If multiple users are monitored, the sleep data may be stored and mapped to a master user account or to the corresponding users' accounts.

Cloud-based server system 170 may additionally or alternatively provide other cloud-based services. For instance, device 101 may additionally function as a home assistant device. A home assistant device may respond to vocal queries from a user. In response to detecting a vocal trigger phrase being spoken via microphone 134, device 101 may record audio. A stream of the audio may be transmitted to cloud-based server system 170 for analysis. Cloud-based server system 170 may perform a speech recognition process, use a natural language processing engine to understand the query from the user, and provide a response to be output by device 101 as synthesized speech, an output to be presented on electronic display 140, and/or a command to be executed by device 101 (e.g., raise the volume of device 101) or sent to some other smart home device. Further, queries or commands may be submitted to cloud-based server system 170 via electronic display 140, which may be a touchscreen. For instance, device 101 may be used to control various smart home devices or home automation devices. Such commands may be sent directly by device 101 to the device to be controlled or may be sent via cloud-based server system 170.

Based on data output by radar processing module 112, sleep state detection engine 114 may be used to determine whether a user is likely asleep or awake. Sleep state detection engine 114 may progress through a state machine, such as detailed in relation to FIG. 4 or may use the state identified using such a state machine to determine whether the user is likely awake or asleep. For example, if a user is determined to be in bed and still for at least a defined period of time, the user may be identified as asleep. The output of sleep state detection engine 114 may be used by environmental event correlation engine 116. Environmental event correlation engine 116 may analyze data received from environmental sensor suite 130. Data from each environmental sensor device may be monitored for: 1) an increase of the environmental condition above a fixed defined threshold; and/or 2) an increase in the environmental condition by at least a predefined amount or percentage. As an example, data indicating the light level in the ambient environment may be continuously or periodically output by light sensor 132. Environmental event correlation engine 116 may determine whether: 1) the ambient amount of lighting has increased from below a fixed defined threshold to above the fixed defined threshold; and/or 2) the ambient amount of lighting has increased by at least a predefined amount of percentage. If options 1, 2, or both occur, it may be determined that an environmental event has occurred. This environmental event may be timestamped by environmental event correlation engine 116. Environmental event correlation engine 116 may then determine whether the user waking can be attributed to the identified environmental event.

The radar data stream output by radar subsystem 120 may be output to human interaction engine 245 in addition to radar processing module 112. Human interaction engine 245 may use the radar data stream to determine if a human interaction, such as a human moving within a defined distance of device 101 or a gesture has been performed. Further detail regarding how radar subsystem 120, radar processing module 112, and human interaction engine 245 function and interact is detailed in relation to FIGS. 2A and 2B.

Figure 2A:
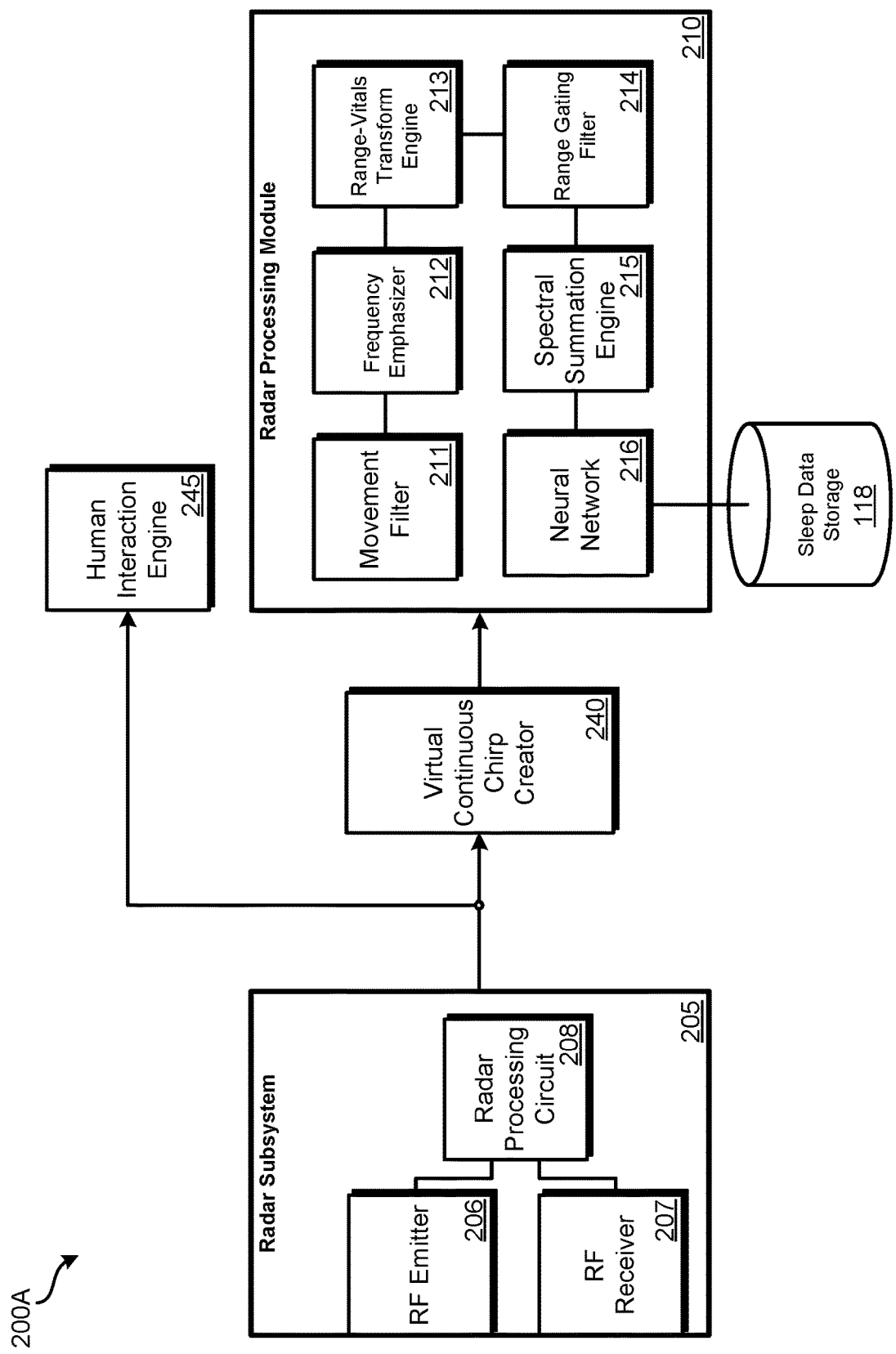
FIG. 2A illustrates an embodiment of a health tracking system that uses radar to detect human interactions and perform health monitoring.

FIG. 2A illustrates an embodiment of a an embodiment of a health monitoring system 200A ("system 200A") that uses radar to detect human interactions and perform health monitoring. System 200A can include radar subsystem 205 (which can represent an embodiment of radar subsystem 120); radar processing module 210 (which can represent an embodiment of radar processing module 112); beam steering module 230; virtual continuous chirp creator 240; and human interaction engine 245.

Radar subsystem 205 may include RF emitter 206, RF receiver 207, and radar processing circuit 208. RF emitter 206 can emit radio waves, such as in the form of continuous-wave (CW) radar. RF emitter 206 may use frequency-modulated continuous-wave (FMCW) radar. The FMCW radar may operate in a continuous sparse-sampling mode over a relatively long period of time. RF emitter 206 may include one or more antennas and may transmit at or about 60 GHz. The frequency of radio waves transmitted may repeatedly sweep from a low to high frequency (or the reverse). The power level used for transmission may be very low such that radar subsystem 205 has an effective range of several meters or an even shorter distance. Further detail regarding the radio waves generated and emitted by radar subsystem 205 are provided in relation to FIG. 2C.

RF receiver 207 includes one or more antennas, distinct from the transmit antenna(s), and may receive radio wave reflections off of nearby objects of radio waves emitted by RF emitter 206. The reflected radio waves may be interpreted by radar processing circuit 208 by mixing the radio waves being transmitted with the reflected received radio waves, thereby producing a mixed signal that can be analyzed for distance. Based on this mixed signal, radar processing circuit 208 may output raw waveform data, which can also be referred to as a raw chirp waterfall for analysis by a separate processing entity. Radar subsystem 205 may be implemented as a single integrated circuit (IC) or radar processing circuit 208 may be a separate component from RF emitter 206 and RF receiver 207. In some embodiments, radar subsystem 205 is integrated as part of device 101 such that RF emitter 206 and RF receiver 207 are pointing in a same direction as display 140. In other embodiments, an external device that includes radar subsystem 205 may be connected with device 101 via wired or wireless communication. For example, radar subsystem 205 may be an add-on device to a home assistant device.

RF subsystem 205 outputs a radar data stream. Since RF subsystem 205 is operated in burst mode, the radar data stream output may be referred to as a burst mode radar data stream. The burst mode radar data stream may be output by radar subsystem 205 to human interaction engine 245 and to virtual continuous chirp creator 240. Human interaction engine 245 and virtual continuous chirp creator 240 may be implemented as software that is executed using the same processing system as radar processing module 210. In other embodiments, a separate processing system may be used for virtual continuous chirp creator 240, human interaction engine 245, or both. In other embodiments, dedicated hardware may be used to perform the functions of virtual continuous chirp creator 240, human interaction engine 245, or both.

Human interaction engine 245 may use the burst mode radar data stream to determine if any human interaction has occurred. The processing performed by human interaction engine 245 may occur independently of the processing performed by virtual continuous chirp creator 240 and radar processing module 210. Therefore, whether or not health monitoring is being performed by radar processing module 210 or a component that uses data output by radar processing module 210 may be irrelevant to human interaction engine 245 monitoring for contactless human interactions, such as presence and gestures. To be clear, "contactless" refers to there being no physical contact between a user and the device on which system 200A is implemented. Rather, remote sensing, such as radar, is used to monitor the user.

Virtual continuous chirp creator 240 also receives the burst mode radar data stream. Virtual continuous chirp creator 240 performs processing on the received burst mode radar data stream and outputs a virtual continuous mode radar data stream. Specifics on the processing performed by virtual continuous chirp creator 240 to create the virtual continuous mode radar data stream is provided in relation to FIG. 6. The output of virtual continuous chirp creator 240 is provided to radar processing module 210. Radar processing module 210 performs processing on the virtual continuous mode radar data stream the same as if a continuous mode radar data stream was output to radar processing module 210 directly by radar subsystem 205.

For radar subsystem 205, if FMCW is used, an unambiguous FMCW range can be defined. Within this range, a distance to objects can be accurately determined. However, outside of this range, a detected object could be incorrectly interpreted as nearer than an object within the unambiguous range. This incorrect interpretation can be due to the frequency of the mixed signal and the sampling rate of the ADC used by the radar subsystem to convert the received analog signals to digital signals. If the frequency of the mixed signal is above the Nyquist rate of the sampling of the ADC, the digital data output by the ADC representative of the reflected radar signal can be incorrectly represented (e.g., as a lower frequency indicative of a closer object).

Radar processing module 210 may include one or more processors. Radar processing module 210 may include one or more special-purpose or general-purpose processors. Special-purpose processors may include processors that are specifically designed to perform the functions detailed herein. Such special-purpose processors may be ASICs or FPGAs which are general-purpose components that are physically and electrically configured to perform the functions detailed herein. General-purpose processors may execute special-purpose software that is stored using one or more non-transitory processor-readable mediums, such as random access memory (RAM), flash memory, a hard disk drive (HDD), or a solid state drive (SSD). Radar processing module 210 may include: movement filter 211; frequency emphasizer 212; range-vitals transform engine 213; range gating filter 214; spectral summation engine 215; and neural network 216. Each of the components of radar processing module 210 may be implemented using software, firmware, or as specialized hardware.

The virtual continuous mode radar data stream from virtual continuous chirp creator 240 may be received by radar processing module 210 and first processed using movement filter 211. In some embodiments, it is important that movement filter 211 is the initial component used to perform filtering. That is, the processing performed by radar processing module 210 is not commutative in some embodiments. Typically, vital sign determination and sleep monitoring may occur when a monitored user is sleeping or attempting to sleep in a bed. In such an environment, there may typically be little movement. Such movement may be attributed to the user moving within the bed (e.g., rolling over while trying to get to sleep or while asleep) and the user's vital signs, including movement due to breathing and movement due to the monitored user's heartbeat. In such an environment, a large portion of emitted radio waves from RF emitter 206 may be reflected by static objects in the vicinity of the monitored user, such as a mattress, box spring, bed frame, walls, furniture, bedding, etc. Therefore, a large portion of the raw waveform data received from radar subsystem 205 may be unrelated to user movements and the user's vital measurements.

Movement filter 211 may include a waveform buffer that buffers "chirps" or slices of received raw waveform data. For instance, sampling may occur at a rate of 10 Hz. In other embodiments, sampling may be slower or faster. Movement filter 211 may buffer twenty seconds of received raw waveform chirps in certain embodiments. In other embodiments, a shorter or longer duration of buffered raw waveform data is buffered. This buffered raw waveform data can be filtered to remove raw waveform data indicative of stationary objects. That is, for objects that are moving, such as a monitored user's chest, the user's heartbeat and breathing rate will affect the distance and velocity measurements made by radar subsystem 205 and output to movement filter 211. This movement of the user will result in "jitter" in the received raw waveform data over the buffered time period. More specifically, jitter refers to the phase shifts caused by moving objects reflecting emitted radio waves. Rather than using the reflected FMCW radio waves to determine a velocity of the moving objects, the phase shift induced by the motion in the reflected radio waves can be used to measure vital statistics, including heartrate and breathing rate, as detailed herein.

For stationary objects, such as furniture, a zero phase shift (i.e., no jitter) will be present in the raw waveform data over the buffered time period. Movement filter 211 can subtract out such raw waveform data corresponding to stationary objects such that motion-indicative raw waveform data is passed to frequency emphasizer 212 for further analysis. Raw waveform data corresponding to stationary objects may be discarded or otherwise ignored for the remainder of processing by radar processing module 210.

In some embodiments, an infinite impulse response (IIR) filter is incorporated as part of movement filter 211. Specifically, a single-pole IIR filter may be implemented to filter out raw waveform data that is not indicative of movement. Therefore, the single-pole IIR filter may be implemented as a high-pass, low-block filter that prevents raw waveform data indicative of movement below a particular frequency from passing through to frequency emphasizer 212. The cut-off frequency may be set based on known limits to human vital signs. For example, a breathing rate may be expected to be between 10 and 60 breaths per minute. Movement data indicative of a lower frequency than 10 breaths per minute may be excluded by the filter. In some embodiments, a band-pass filter may be implemented to exclude raw waveform data indicative of movement at high frequencies that are impossible or improbable for human vital signs. For instance, a heartrate, which can be expected to be above a breathing rate, may be unlikely to be above 150 beats per minute for a person in a resting or near-resting state. Raw waveform data indicative of a higher frequency may be filtered out by the band pass filter.

In some embodiments, it may be possible to further fine-tune the frequencies of raw waveform data that movement filter 211 passes to frequency emphasizer 212. For instance during an initial configuration phase, a user may provide information about the monitored user (e.g., himself, a child), such as age data. Table 1 indicates typical respiratory rates for various ages. Similar data may be present for heartrate. The filter may be configured to exclude data that is outside of the expected breathing rate, heartrate range, or both.

TABLE 1

| Age | Breathing Rate Range (breaths per minute) |
| --- | --- |
| Birth-6 weeks | 30-60 |
| 6 months | 25-40 |
| 3 years | 20-30 |
| 6 years | 18-25 |
| 10 years | 17-23 |
| Adults | 12-18 |
| 65-80 years old | 12-28 |
| >80 years old | 10-30 |

The vital signs of the monitored user being measured are periodic impulse events: a user's heartrate may vary over time, but it can be expected that the user's heart will continue to beat periodically. This beating is not a sinusoidal function, but rather may be understood as an impulse event, more analogous to a square wave having a relatively low duty cycle that induces motion in the user's body. Similarly, a user's breathing rate may vary over time, but breathing is a periodic function performed by the user's body that is analogous to sinusoidal function, except that a user's exhale is typically longer than their inhale. Further, at any given time, a particular window of waveform data is being analyzed. Since a particular time window of waveform data is being analyzed, even a perfect sinusoid within that window can result in spectral leakage in the frequency domain. Frequency components due to this spectral leakage should be deemphasized.

Frequency emphasizer 212 may work in conjunction with range-vitals transform engine 213 to determine the one (e.g., breathing) or two (e.g., breathing plus heartbeat) frequency components of the raw waveform data. Frequency emphasizer 212 may use frequency windowing, such as a 2D Hamming window (other forms of windowing are possible, such as a Hann window), to emphasize important frequency components of the raw waveform data and to deemphasize or remove waveform data that is attributable to spectral leakage outside of the defined frequency window. Such frequency windowing may decrease the magnitude of raw waveform data that is likely due to processing artifacts. The use of frequency windowing can help reduce the effects of data-dependent processing artifacts while preserving data relevant for being able to separately determine heartrate and breathing rate.

For a stationary bedside FMCW radar-based monitoring device, which may be positioned within 1 to 2 meters of the one or more users being monitored to detect breathing and heartrate (e.g., using radar as emitted in FIG. 2C), a 2D Hamming window that emphasizes frequencies in the range of 10 to 60 bpm (0.16 Hz to 1 Hz) for breathing and 30 to 150 bpm (0.5 to 2.5 Hz) for heartbeat provide for sufficiently good signals to make reliable measurements without requiring advance knowledge of the subject's age or medical history.

Since heartrate and breathing rate are periodic impulse events, the frequency domain heartrate, and breathing rate may be represented by different fundamental frequencies, but each may have many harmonic components at higher frequencies. One of the primary purposes of frequency emphasizer 212 may be to prevent the frequency ripples of harmonics of the monitored user's breathing rate from affecting the frequency measurement of the monitored user's heartrate (or the reverse). While frequency emphasizer 212 may use a 2D Hamming window, it should be understood that other windowing functions or isolating functions can be used to help isolate frequency ripples of the monitored user's breathing rate from the frequency ripples of the monitored user's heartrate.

Range-vitals transform engine 213 analyzes the received motion-filtered waveform data to identify and quantify the magnitude of movement at specific frequencies. More particularly, range-vitals transform engine 213 analyzes phase jitter over time to detect relatively small movements due to a user's vital signs that have a relatively low frequency, such as breathing rate and heart rate. The analysis of range-vitals transform engine 213 may assume that the frequency components of the motion waveform data are sinusoidal. Further, the transform used by range-vitals transform engine 213 can also identify the distance at which the frequency is observed. Frequency, magnitude, and distance can all be determined at least in part because radar subsystem 205 uses an FMCW radar system.

Prior to applying the transform of range-vitals transform engine 213, a zero-padding process may be performed by range-vitals transform engine 213 to add a number of zeros to the motion-filtered raw waveform data. By performing a zero-padding process, the resolution within the frequency domain can be increased effectively, allowing for more accurate low-rate measurements (e.g., a low heartrate, a low breathing rate). For example, zero-padding can help numerically increase resolution to detect differences of half a breath per minute compared to a resolution of a breath per minute without zero-padding. In some embodiments, three to four times the number of zeros compared to the buffered sample size of the raw waveform data may be added. For example, if twenty seconds of buffered raw waveform data are analyzed, sixty to eighty seconds' worth of zero padding may be added to the sample. Specifically, the range of three to four times zero padding of the sample was found to substantially increase resolution while not making the transform process overly complex (and, thus, processor use-intensive).

In order to determine the amount of zero padding to be performed, equations 1-3 may be used. In equation 1, RPM_resolution may ideally be less than 1.

$$RPM_{resolution} = 60 * \frac{chirp\_rate}{n\_fft\_slow\_time} \quad \text{Eq. 1}$$

$$n\_FFT\_slow\_time\_min = (nearest\_power\_of\_2)(60*chirp\_rate) \quad \text{Eq. 2}$$

In some embodiments, a chirp rate (chirp_rate) of 30 Hz may be used. Such a frequency may have sufficient margin from Nyquist limits of the upper limit of breathing rate and heartbeat rate. n_FFT_slow_time_min may, therefore, be 2048. Given a 20 second window for estimating respiration statistics, Equation 3 results in a value of 600.

$$n\_chirps\_for\_respiration = 20*chirp\_rate = 600 \quad \text{Eq. 3}$$

This value of 600 is smaller than the required vitals-FFT size and makes range-vitals transform engine 213 perform a 3× to 4× zero padding. A balance in how much zero padding to perform may be based on increasing the frequency resolution and associated increases in the amount of computation needed to perform the FFT. A 3× to 4× zero padding has been found to provide sufficient resolution for heartrate and breath rate while moderating the amount of computation needing to be performed.

Range-vitals transform engine 213 can perform a series of Fourier transform (FT) to determine the frequency components of the received raw waveform data output by frequency emphasizer 212. Specifically, a series of fast Fourier transform (FFT) may be performed by range-vitals transform engine 213 to determine the specific frequencies and magnitudes of waveform data at such frequencies.

Waveform data obtained over a period of time can be expressed in multiple dimensions. A first dimension (e.g., along the y-axis) can relate to multiple samples of waveform data from a particular chirp and a second dimension (e.g., along the x-axis) relates to a particular sample index of waveform data gathered across multiple chirps. A third dimension of data (e.g., along the z-axis) is present indicative of the intensity of the waveform data.

Multiple FFTs may be performed based on the first and second dimension of the waveform data. FFTs may be performed along each of the first and second dimensions: an FFT may be performed for each chirp and an FFT may be performed for each particular sample index across multiple chirps that occurred during the period of time. An FFT performed on waveform data for a particular reflected chirp can indicate one or more frequencies, which, in FMCW radar, are indicative of the distances at which objects are present that reflected emitted radio waves. An FFT performed for a particular sample index across multiple chirps can measure the frequency of phase jitter across the multiple chirps. Therefore, the FFT of the first dimension can provide the distance at which a vital statistic is present and the FFT of the second dimension can provide a frequency of the vital statistic. The output of the FFTs performed across the two dimensions is indicative of: 1) the frequencies of vital statistics; 2) the ranges at which the vital statistics were measured; and 3) the magnitudes of the measured frequencies. In addition to values due to vital statistics being present in the data, noise may be present that is filtered, such as using spectral summation engine 215. The noise may be partially due to heartrate and breathing not being perfect sinusoidal waves.

To be clear, the transform performed by range-vitals transform engine 213 differs from a range-Doppler transform. Rather than analyzing changes in velocity (as in a range-Doppler transform), periodic changes in phase shift over time are analyzed as part of the range-vitals transform. The range-vitals transform is tuned to identify small movements (e.g., breathing, heart rate) occurring over a relatively long period of time by tracking changes in phase, referred to as phase jitter. As previously detailed, zero padding is performed to allow for sufficient resolution for accurate determination of heartrate and breathing rate.

Range gating filter 214 is used to monitor a defined range of interest and exclude waveform data due to movement beyond the defined range of interest. For arrangements detailed herein, the defined range of interest may be 0 to 1 meter. In some embodiments, this defined range of interest may be different or possibly set by a user (e.g., via a training or setup process) or by a service provider. In some embodiments, a goal of this arrangement may be to monitor the one person closest to the device (and exclude or segregate data for any other person farther away, such as a person sleeping next to the person being monitored). In other embodiments, if both persons are to be monitored, the data may be segregated, as detailed in relation to FIG. 12. Therefore, range-vitals transform engine 213 and range gating filter 214 serve to segregate, exclude, or remove movement data attributed to objects outside of the defined range of interest and sum the energy of movement data attributed to objects within the defined range of interest. The output of range gating filter 214 may include data that has a determined range within the permissible range of range gating filter 214. The data may further have a frequency dimension and a magnitude. Therefore, the data may possess three dimensions.

Spectral summation engine 215 may receive the output from range gating filter 214. Spectral summation engine 215 may function to transfer the measured energy of harmonic frequencies of the heartrate and breathing rate and sum the harmonic frequency energy onto the fundamental frequency's energy. This function can be referred to as a harmonic sum spectrum (HSS). Heartrate and breathing rate are not sinusoidal; therefore, in the frequency domain, harmonics will be present at frequencies higher than the fundamental frequency of the user's breathing rate and the fundamental frequency of the user's heartrate. One of the primary purposes of spectral summation engine 215 is to prevent harmonics of the monitored user's breathing rate from affecting the frequency measurement of the monitored user's heartrate (or the reverse). The HSS may be performed at the second order by summing the original spectrum with a down-sampled instance (by a factor of two) of the spectrum. This process may also be applied at higher order harmonics such that their respective spectra are added to the spectrum at the fundamental frequency.

At this stage, for a person in bed who is lying still (with the exception of movement due to breathing and heartrate), it will be expected that two major frequency peaks will present in the frequency data. However, if the monitored user is physically moving, such as rolling over in bed, the energy will be significantly distributed across the frequency spectrum (a broader distribution). Such large physical movement may manifest itself in the frequency data as being a large number of small peaks. If the bed is empty, rather than a person being present, there may be no or almost no frequency components above the noise floor since movement filter 211 has previously filtered raw waveform data corresponding to static objects. The distribution and magnitude of frequency peaks across the spectrum may be used to determine if the user is likely awake or asleep.

Spectral summation engine 215 may output a feature vector that is indicative of heartrate (e.g., in beats per minute) and breathing rate (e.g., in breaths per minute). The feature vector can indicate frequency and magnitude. Neural network 216 may be used to determine whether the heartrate and/or breathing rate indicated in the output of the feature vector from spectral summation engine 215 should be considered valid. Therefore, the heartrate and breathing rate output by spectral summation engine 215 may be stored, presented to a user, and/or treated as valid based on the output of neural network 216. Neural network 216 may be trained (e.g., using supervised learning performed using a training set of data) to output one of three states, such as those indicated in Table 2 by performing a spectral analysis. Vital statistic data may be considered valid when the user is determined to be present and the detected movement is due to the user's vital signs.

Each state in Table 2 is associated with a different spectral energy and spectral sparsity profile. Spectral energy refers to a summation of the energy across the frequency spectrum detected due to motion being present within the monitored region. Spectral sparsity represents whether movement tends to be distributed across a wide range of frequencies or clustered at a few specific frequencies. For instance, if energy peaks occur at few frequencies, such as when the user's vital signs are detected (but not other movement), spectral sparsity is high. However, if peaks (over a threshold value) or some other form of determination based on a threshold criterion at least partially based on magnitude) occur at many frequencies, spectral sparsity is low.

As an example, motion due to a vital sign, such as a heartbeat, may be indicative of significant movement (e.g., high spectral energy) at specific frequencies (e.g., high spectral sparsity); motion due to a user moving a limb may also be indicative of significant movement (high spectral energy), but may have low spectral sparsity. The neural network may be trained to distinguish between each state based on the spectral energy profile output by spectral summation engine 215. Therefore, neural network 216 may be provided two features, a first value representing spectral energy and a second value representing spectral sparsity.

The output of spectral summation engine 215 may be characterized as a feature vector having a first dimension of frequency and a second dimension of amplitude. The first value representing spectral energy may be calculated by determining the maximum amplitude present in the feature vector output by spectral summation engine 215. This maximum amplitude value may be normalized to a value within 0 to 1. The second value representing the spectral sparsity may be calculated by subtracting the median amplitude of the feature vector from the maximum amplitude. Again here, the calculated sparsity may be normalized to a value within 0 to 1.

Table 2 represents a generalization of how the features of spectral energy and spectral sparsity is used as features by the trained neural network to classify the state of the monitored region.

TABLE 2

| State of Monitored Region | Spectral Energy | Spectral Sparsity |
| --- | --- | --- |
| User present and vitals-only movement | High | High |
| User present and moving (limb and torso movements) | High | Low |
| No user present | Low | Low |

The state of the monitored region classified by neural network 216 may be used in determining the monitored user's sleep state or, more generally, whether the user is moving or still within bed. The state of the monitored region as determined by the performed classification of neural network 216 may further be used to determine if the vital statistics output by spectral summation engine 215 should be trusted or ignored. For accurate vital statistic determination, heartrate and breathing rate may be identified as likely accurate when neural network 216 determines that the user is present and still (i.e., no large physical movements; however, movement is occurring due to breathing and/or heartbeat). In some embodiments, the vital statistics output by spectral summation engine 215 may be exclusively stored locally (e.g., to alleviate privacy concerns); in other embodiments, the vital statistics output may be transmitted to cloud-based server system 170 for remote storage (in alternative or in addition to such data being stored locally).

Neural network 216 may be initially trained using a large set of training data of amplitude and frequency feature vectors that have been properly tagged with a classification as mapping the spectral energy and the spectral sparsity to the corresponding ground-truth state of the monitored region. Alternatively, neural network 216 may be initially trained using a large set of training data of amplitude and frequency feature vectors that has been properly classified as mapping the comprising spectral energy and the spectral sparsity pairs each properly tagged to the corresponding ground-truth state of the monitored region. The neural network may be a fully connected neural network that is not time-dependent. In some embodiments, a machine-learning arrangement, classifier, or form of artificial intelligence other than a neural network may be used.

In other embodiments, rather than a spectral energy value and a spectral sparsity value being the features used by the neural network, a neural network, possibly with extra front-end convolutional layers, can be trained to use the output of range gating filter 214 directly. Rather, an embodiment of a convolutional network can analyze the frequency and magnitude data output by range gating filter 214 to classify the state of the user. The convolutional neural network may be trained to utilize offline training that is based on a set of spectral measurements mapped to the ground truth state of the monitored region prior to system 200B being used by an end user.

The sleep state determined by neural network 216 may be stored, along with time data, to sleep data storage 118. The vital statistics output by spectral summation engine 215 can be stored to a vital statistic datastore when neural network 216 indicates that the monitored user is present and still. Other vital statistic data may be discarded or possibly flagged to indicate it is less likely to be correct. The data stored to sleep data storage 118 and a vital statistic datastore may be stored locally at device 101. In some embodiments, storage occurs at only device 101. Such an implementation may help alleviate a concern about health-related data being transmitted and stored remotely. In some embodiments, the monitored user may elect to have sleep data and vital statistic data transmitted via a network interface (e.g., wireless network interface 150), stored, and analyzed externally, such as by cloud-based server system 170. Storage by cloud-based server system 170 may have significant benefits, such as the ability for the user to access such data remotely, allow access to a medical provider, or participate in research studies. The user may retain the ability to delete or otherwise remove the data from cloud-based server system 170 at any time.

In some embodiments, radar processing module 210 may be wholly or partly located remotely from device 101. While radar subsystem 205 may need to be local to the monitored user, the processing of radar processing module 210 may be moved to cloud-based server system 170. In other embodiments, a smart home device that is in local communication (e.g., via a LAN or WLAN) with device 101 may perform some or all of the processing of radar processing module 210. In some embodiments, a local communication protocol, such as involving a mesh network, can be used to transmit the raw waveform data to the local device that will be performing the processing. Such communication protocols can include Wi-Fi, Bluetooth, Thread, or communication protocols of the IEEE 802.11 and 802.15.4 families. Similar to the processing, storage of the sleep data and vital statistic data may occur at cloud-based server system 170 or another smart home device in the home at which device 101 is located. In still other embodiments, radar processing module 210 may be incorporated with radar subsystem 205 as a single component or system of components.

The stored sleep data of sleep data storage 118 and the vital statistic data may be used to provide the user with short-term and long-term trends relating to their sleeping patterns, vital statistics, or both by sleep data compilation engine 119. For instance, each morning, graphs, statistics, and trends may be determined by sleep data compilation engine 119 based on data stored to sleep data storage 118 and output for display by sleep data compilation engine 119 via display 140. A graph that is indicative of sleep data from the previous night and possibly one or more graphs indicative of breathing rates and heartrate during the previous night may be presented. Similar graphs, trends, and statistics may be output for significantly longer periods of time, such as weeks, months, years, and even multi-year stretches of time by sleep data compilation engine 119. Other uses for sleep data and vital statistics may be possible. For instance, if certain triggers regarding heartrate, breathing rate, and/or sleeping patterns are triggered, a medical professional may be notified. Additionally or alternatively, a notification may be output to the user indicating that the collected data is potentially concerning or is indicative of a healthy person. In some instances, specific sleep problems may be identified, such as sleep apnea. Sleep data may be output via speaker 155 using synthesized speech (e.g., in response to the user waking, in response to a spoken user command, or in response to a user providing input via a touchscreen, such as display 140). Such sleep data may also be represented graphically and or textually on display 140.

System 200A may additionally include beam steering module 230. Beam steering module 230 may include channel weighting engine 231, which may be implemented similarly to the components of radar processing module 210 using software, firmware, and/or hardware. Beam steering module 230 is illustrated as separate from radar processing module 210 because it processes data received from radar subsystem 205 to emphasize data received from a particular direction and deemphasize data received from other directions. Beam steering module 230 may be implemented using the same hardware as radar processing module 210. For instance, beam steering module 230 may be a software process that modifies the radar data received from radar subsystem 205 prior to movement filter 211 being applied. Device 101 may be a surface-top device that is intended to be placed in a particular location, connected with a continuous power supply (e.g., a household power outlet) and interacted with via voice and/or a touchscreen. Therefore, radar subsystem 205 may remain pointed at a portion of the ambient environment for significant periods of time (e.g., multiple hours, days, weeks, months). Generally speaking, beam steering module 230 may be used to map the environment (e.g., room) in which device 101 is located and steer the sensing direction of radar subsystem 205 to a zone within the field-of-view of radar subsystem 205 most likely to have a user present.

Targeting the region within the field-of-view of radar subsystem 205 may help decrease an amount of false negatives and positives caused by movement of objects other than a user. Further, targeting can help compensate for an angle and location of device 101 relative to where the user sleeps. (For instance, device 101 may be located on a nightstand that is at a different height than the user's bed. Additionally or alternatively, radar subsystem 205 device 101 might not be pointed directly at the location in the bed where the user sleeps.)

When no user is determined to be present, such as based on low spectral energy and low spectral density of Table 2, an optimal beam steering process may be performed by channel weighting engine 231 and beam steering system 232. While no user is present, an analysis can be performed to determine which directional alignment of radar subsystem 205 provides minimal-clutter.

Figure 2B:
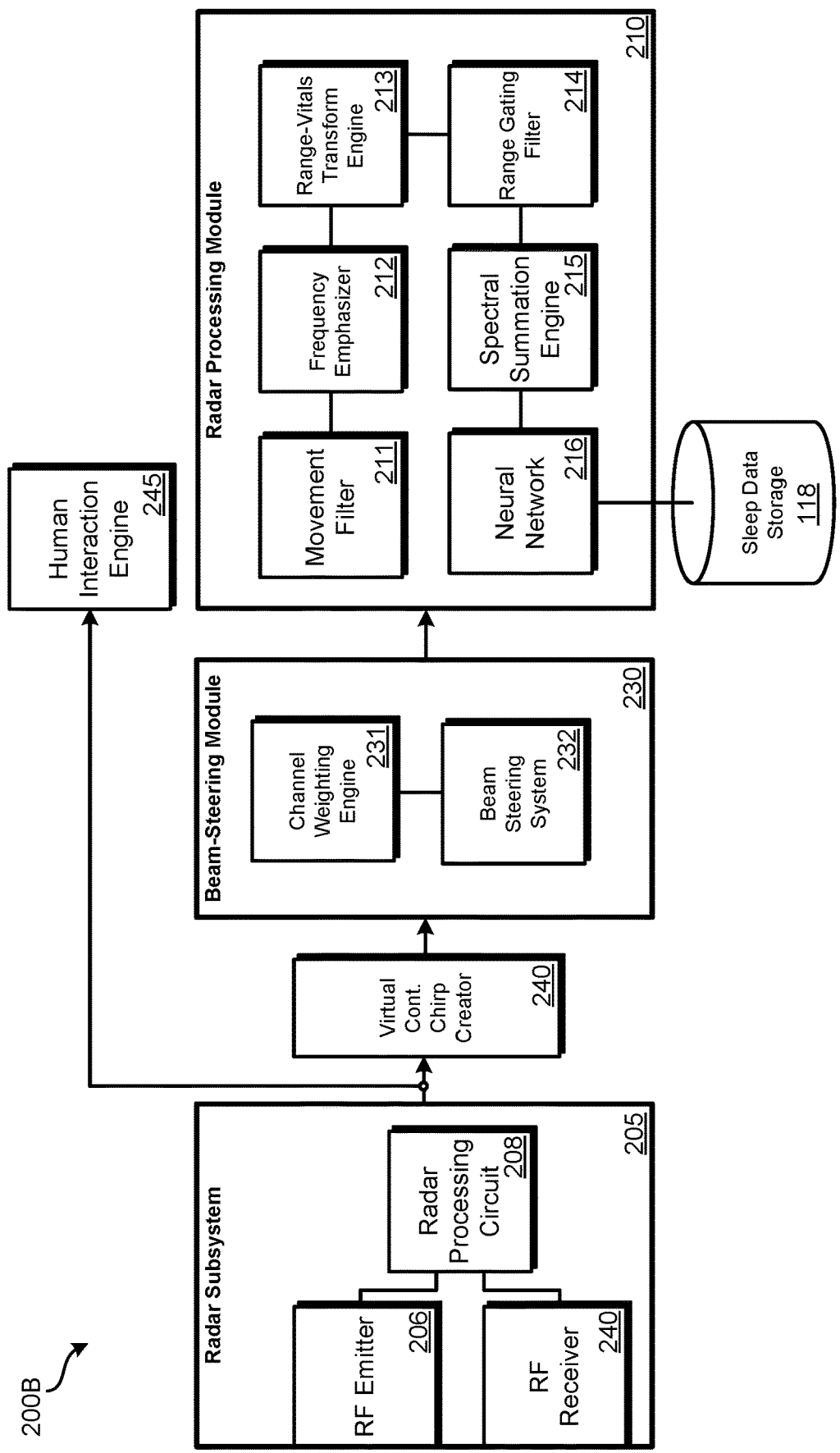
FIG. 2B illustrates an embodiment of a health tracking system that uses radar to detect human interactions and perform health monitoring with integrated beam targeting.

FIG. 2B illustrates an embodiment of a health tracking system 200B ("system 200B") that uses radar to detect human interactions and perform health monitoring with integrated beam targeting. Beam targeting performed by using beam steering module 230 can focus on radar reflections from a region in which a user may be present and ignore or at least decrease the use of radar reflections from objects that cause interference, such as a nearby wall or large object. Notably, beam steering module 230 may perform processing on the virtual continuous mode radar data stream; therefore, the burst mode radar data stream analyzed by human interaction engine 245 can be unaffected by the targeting performed by beam steering module 230.

Virtual continuous chirp creator 240 and human interaction engine 245 may function as detailed in relation to FIG. 2A. However, the virtual continuous mode radar stream output by virtual continuous chirp creator 240 is input to beam steering module 230 instead of directly to radar processing module 210. Radar subsystem 205 may output separate data for each antenna of radar subsystem 205. Therefore, a separate burst mode radar data stream may be present for each antenna (or within a single burst mode radar data stream, the particular antenna that received the reflected radio waves may be indicated). Virtual continuous chirp creator 240 may maintain the separate of data for each antenna. Therefore, virtual continuous mode radar data streams may be created for each antenna or a single virtual continuous mode radar data stream may be created that indicates what portions of the virtual continuous mode radar data stream correspond to which antenna of radar subsystem 205.

Radar subsystem 205 may contain multiple antennas to receive reflected radar radio waves. In some embodiments, three antennas may be present. These antennas may be aligned in an "L" pattern, such that two antennas are horizontally orthogonal and two antennas are vertically orthogonal with one of the antennas being used in both the horizontal arrangement and vertical arrangement. By analyzing the phase difference in received radar signals, a weighting may be applied to target the received radar beam vertically and/or horizontally. In other embodiments, the antennas may be aligned in a different pattern.

Vertical targeting may be performed to compensate for a vertical tilt of the device in which system 200B is incorporated. For instance, as discussed below in relation to FIG. 3A, the face of contactless health tracking device 300 may be tilted with respect to where a user will typically be sleeping.

Horizontal targeting may be performed to compensate for emitted radar being pointed towards an object that causes interference. For instance, if a user's bed headboard is against a wall, the headboard and/or wall may occupy a significant portion of the field-of-view of radar subsystem 120. Radar reflections from the headboard and/or wall might not be useful in determining data about the user; therefore, it may be beneficial to deemphasize reflections from the wall and/or headboard and emphasize reflections obtained away from the wall and/or headboard. Therefore, the receive beam may be steered horizontally away from the wall and the headboard by weighting applied to the received radar signals.

In system 200B, beam steering module 230 is present to perform processing on the raw chirp waterfall of the virtual continuous mode radar data stream received from radar subsystem 205 via virtual continuous chirp creator 240. Therefore, beam steering module 230 can function as a preprocessing module prior to the analysis of radar processing module 210 and can serve to emphasize regions where one or more users are expected to be present. Beam steering module 230 may be implemented using hardware, software, or firmware; therefore, beam steering module 230 may be implemented using the same one or more processors as radar processing module 210.

Beam steering module 230 can include channel weighting engine 231 and beam steering system 232. Channel weighting engine 231 can be used to perform a training process to determine a series of weightings to be applied to received radar signals from each antenna prior to the received radar signals being mixed together. Channel weighting engine 231 may perform a training process when a monitored region is determined to be empty. During such time, the strength of signals received from large static objects (e.g., walls, headboards) can be analyzed and weightings can be set to steer the beam horizontally (and possibly vertically) away from such objects. Therefore, the amount of reflection in a static environment may be minimized for a particular distance range (e.g., up to one meter) from the device by channel weighting engine 231 steering the receive radar beam. Such training may also be performed when a user is present. That is, the receive beam of radar subsystem 205 can be steered to where motion is detected, or specifically, vital signs of a user are present.

The weightings determined by channel weighting engine 231 may be used by beam steering system 232 to individually apply a weight to the received reflected radar signals of each antenna. The received signals from each antenna may be weighted then mixed together for processing by radar processing module 210.

Figure 2C:
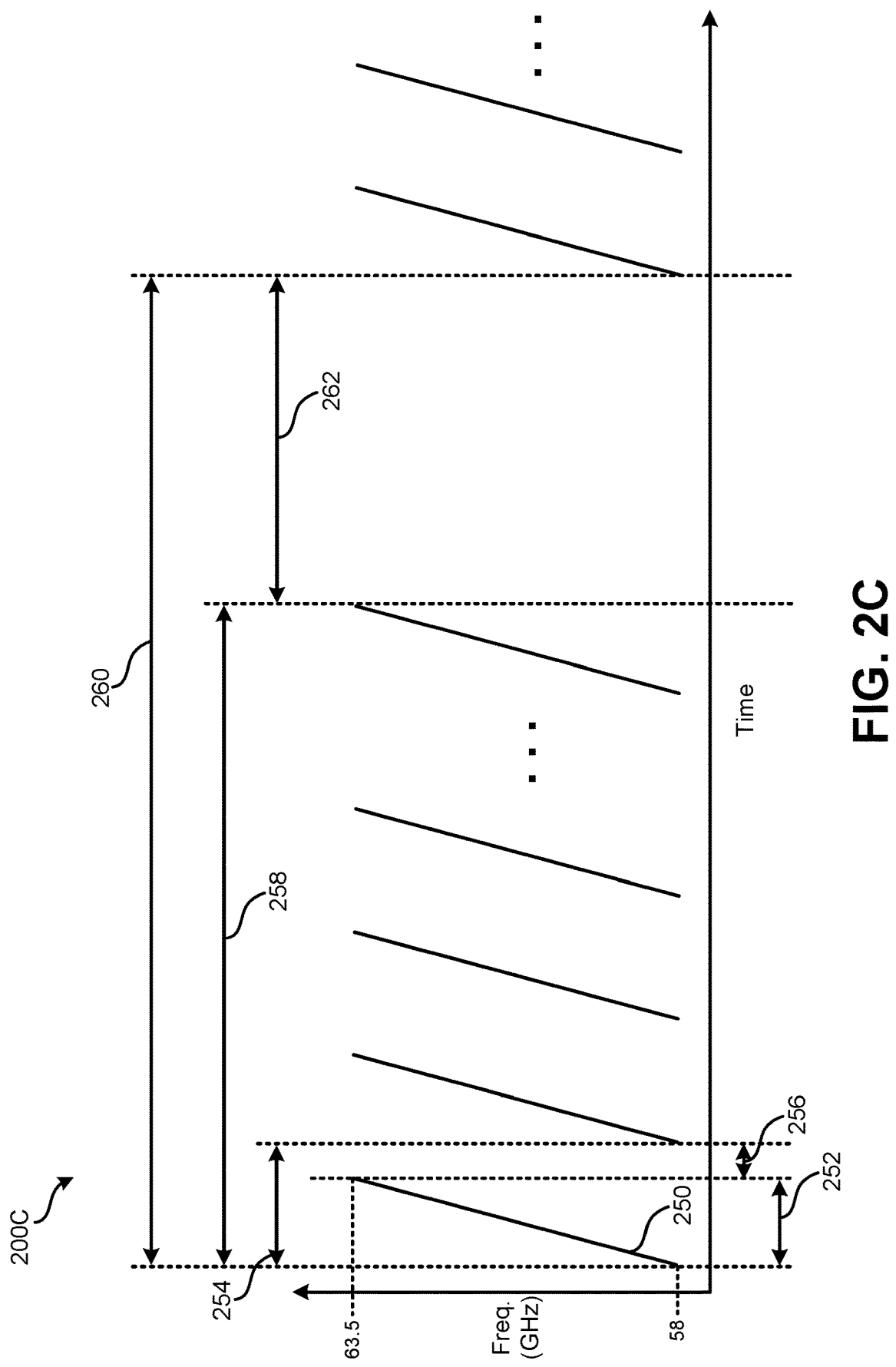
FIG. 2C illustrates an embodiment of frequency-modulated continuous wave radar radio waves output by a radar subsystem.

FIG. 2C illustrates an embodiment of chirp timing diagram 200C for frequency modulated continuous wave (FMCW) radar radio waves output by a radar subsystem. Chirp timing diagram 200C is not to scale. Radar subsystem 205 may generally output radar in the pattern of chirp timing diagram 200C. Chirp 250 represents a continuous pulse of radio waves that sweeps up in frequency from a low frequency to a high frequency. In other embodiments, individual chirps may continuously sweep down from a high frequency to a low frequency, from a low frequency to a high frequency, and back to a low frequency, or from a high frequency to a low frequency and back to a high frequency. In some embodiments, the low frequency is 58 GHz and the high frequency is 63.5 GHz. (For such frequencies, the radio waves may be referred to as millimeter waves.) In some embodiments, the frequencies are between 57 and 64 GHz. The low frequency and the high frequency may be varied by embodiment. For instance, the low frequency and the high frequency may be between 45 GHz and 80 GHz. The frequencies select may be selected at least in part to comply with governmental regulation. In some embodiments, each chirp includes a linear sweep from a low frequency to a high frequency (or the reverse). In other embodiments, an exponential or some other pattern may be used to sweep the frequency from low to high or high to low.

Chirp 250, which can be representative of all chirps in chirp timing diagram 200C, may have chirp duration 252 of 128 μs. In other embodiments, chirp duration 252 may be longer or shorter, such as between 50 μs and 1 ms. In some embodiments, a period of time may elapse before a subsequent chirp is emitted. Inter-chirp pause 256 may be 205.33 μs. In other embodiments, inter-chirp pause 256 may be longer or shorter, such as between 10 μs and 1 ms. In the illustrated embodiment, chirp period 254, which includes chirp 250 and inter-chirp pause 256, may be 333.33 μs. This duration varies based on the selected chirp duration 252 and inter-chirp pause 256.

A number of chirps that are output, separated by inter-chirp pauses may be referred to as frame 258 or frame 258. Frame 258 may include twenty chirps. In other embodiments, the number of chirps in frame 258 may be greater or fewer, such as between 1 and 100. The number of chirps present within frame 258 may be determined based upon an average amount of power that is desired to be output within a given period of time. The FCC or other regulatory agency may set a maximum amount of power that is permissible to be radiated into an environment. For example, a duty cycle requirement may be present that limits the duty cycle to less than 10% for any 33 ms time period. In one particular example in which there are twenty chirps per frame, each chirp can have a duration of 128 us, and each frame being 33.33 ms in duration. The corresponding duty cycle is (20 frames)*(0.128 ms)/(33.33 ms), which is about 7.8%. By limiting the number of chirps within frame 258 prior to an inter-frame pause, the average output power may be limited. In some embodiments, the peak EIRP (effective isotropically radiated power) may be 13 dBm (20 mW) or less, such as 12.86 dBm (19.05 mW). In other embodiments, the peak EIRP is 15 dBm or less and the duty cycle is 15% or less. In some embodiments, the peak EIRP is 20 dBm or less. That is, at any given time, the average power radiated over a period of time by the radar subsystem might be limited to never exceed such values. Further, the total power radiated over a period of time may be limited. In some embodiments, a duty cycle may not be required.

Frames may be transmitted at a frequency of 30 Hz (33.33 ms) as shown by time period 260. In other embodiments, the frequency may be higher or lower. The frame frequency may be dependent on the number of chirps within a frame and the duration of inter-frame pause 262. For instance, the frequency may be between 1 Hz and 50 Hz. In some embodiments, chirps may be transmitted continuously, such that the radar subsystem outputs a continuous stream of chirps interspersed with inter-chirp pauses. Tradeoffs can be made to save on the average power consumed by the device due to transmitting chirps and processing received reflections of chirps. Inter-frame pause 262 represents a period of time when no chirps are output. In some embodiments, inter-frame pause 262 is significantly longer than the duration of frame 258. For example, frame 258 may be 6.66 ms in duration (with chirp period 254 being 333.33 μs and 20 chirps per frame). If 33.33 ms occur between frames, inter-frame pause 262 may be 26.66 ms. In other embodiments, the duration of inter-frame pause 262 may be larger or smaller, such as between 15 ms and 40 ms.

In the illustrated embodiment of FIG. 2C, a single frame 258 and the start of a subsequent frame are illustrated. It should be understood that each subsequent frame can be structured similarly to frame 258. Further, the transmission mode of the radar subsystem may be fixed. That is, regardless of whether a user is present or not, the time of day, or other factors, chirps may be transmitted according to chirp timing diagram 200C. Therefore, in some embodiments, the radar subsystem always operates in a single transmission mode, regardless of the state of the environment or the activity attempting to be monitored. A continuous train of frames similar to frame 258 may be transmitted while device 101 is powered on.

Figure 3A:
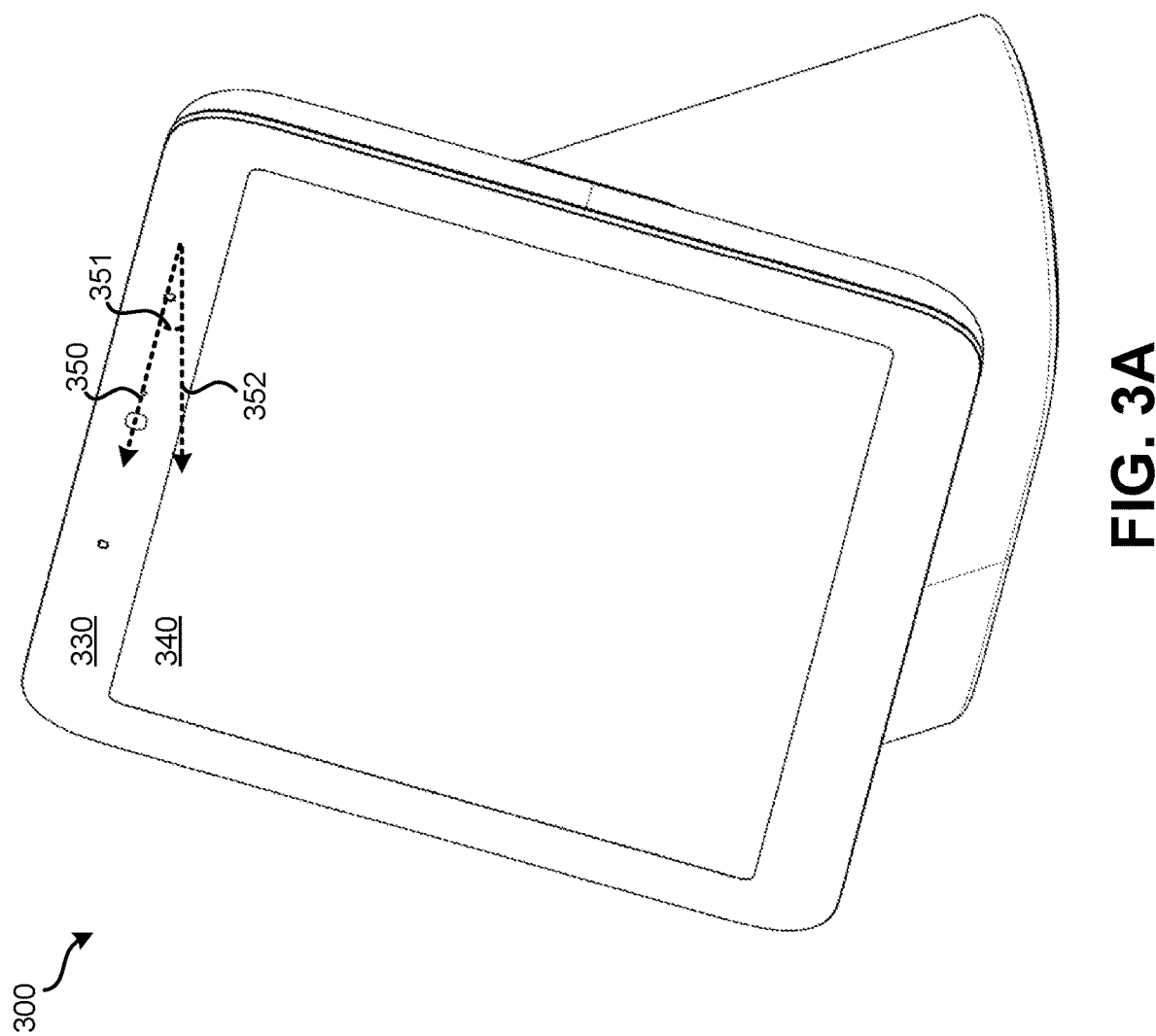
FIG. 3A illustrates an embodiment of a contactless health tracking device.

FIG. 3A illustrates an embodiment of a contactless sleep tracking device 300 ("device 300"). Device 300 may have a front surface that includes a front transparent screen 340 such that a display is visible. Such a display may be a touchscreen. Surrounding front transparent screen 340 may be an optically-opaque region, referred to as bezel 330, through which radar subsystem 205 may have a field-of-view of the environment in front of device 300.

For purposes of the immediate following description, the terms vertical and horizontal describe directions relative to the bedroom in general, with vertical referring to a direction perpendicular to the floor and horizontal referring to a direction parallel to the floor. Since the radar subsystem, which may be an Infineon® BGT60 radar chip, is roughly planar and is installed generally parallel to bezel 330 for spatial compactness of the device as a whole, and since the antennas within the radar chip lie in the plane of the chip, then, without beam targeting, a receive beam of radar subsystem 120 may be pointed in direction 350 that is generally normal to bezel 330. Due to a departure tilt of bezel 330 away from a purely vertical direction, which is provided in some embodiments to be about 25 degrees in order to facilitate easy user interaction with a touchscreen functionality of the transparent screen 340, direction 350 may point upwards from horizontal by departure angle 351. Assuming device 300 will typically be installed on a bedside platform (e.g., nightstand) that is roughly the same height as the top of a mattress on which a user will sleep, it may be beneficial for the receive beam of radar subsystem 120 to be targeted in horizontal direction 352 or an approximately horizontal (e.g., between −5° and 5° from horizontal) direction. Therefore, vertical beam targeting can be used to compensate for departure angle 351 of the portion of device 300 in which radar subsystem 120 is present.

Figure 3B:
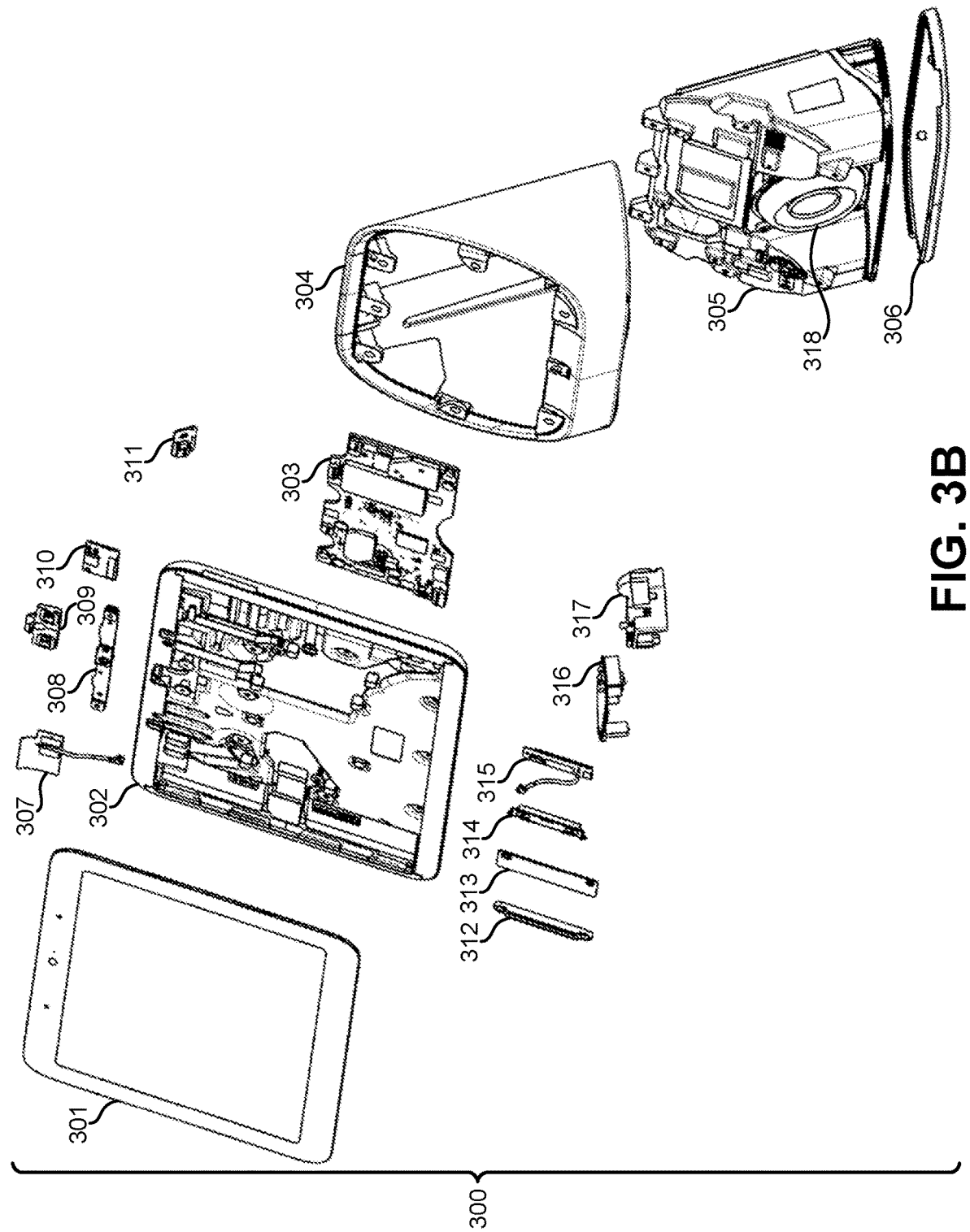
FIG. 3B illustrates an exploded view of an embodiment of a contactless health tracking device.

FIG. 3B illustrates an exploded view of an embodiment of contactless sleep tracking device 300. Device 300 can include: display assembly 301; display housing 302; main circuit board 303; neck assembly 304; speaker assembly 305; base plate 306; mesh network communication interface 307; top daughterboard 308; button assembly 309; radar assembly 310; microphone assembly 311; rocker switch bracket 312; rocker switch board 313; rocker switch button 314; Wi-Fi assembly 315; power board 316; and power bracket assembly 317. Device 300 can represent an embodiment of how device 101 may be implemented.

Display assembly 301, display housing 302, neck assembly 304, and base plate 306 may collectively form a housing that houses all of the remaining components of device 300. Display assembly 301 may include an electronic display, which can be a touchscreen, that presents information to a user. Display assembly 301 may, therefore, include a display screen, which can include a metallic plate of the display that can serve as a grounding plane. Display assembly 301 may include transparent portions away from the metallic plate that allow various sensors a field of view in the general direction in which display assembly 301 is facing. Display assembly 301 may include an outer surface made of glass or transparent plastic that serves as part of the housing of device 300.

Display housing 302 may be a plastic or other rigid or semi-rigid material that serves as a housing for display assembly 301. Various components, such as main circuit board 303; mesh network communication interface 307; top daughterboard 308; button assembly 309; radar assembly 310; and microphone assembly 311 may be mounted on display housing 302. Mesh network communication interface 307; top daughterboard 308; radar assembly 310; and microphone assembly 311 may be connected to main circuit board 303, using flat wire assemblies. Display housing may be attached with display assembly 301, using an adhesive.

Mesh network communication interface 307 may include one or more antennas and may enable communication with a mesh network, such as a Thread-based mesh network. Wi-Fi assembly 315 may be located a distance from mesh network communication interface 307 to decrease the possibility of interference. Wi-Fi assembly 315 may enable communication with a Wi-Fi based network.

Radar assembly 310, which can include radar subsystem 120 or radar subsystem 205, may be positioned such that its RF emitter and RF receiver are away from the metallic plate of display assembly 301 and are located a significant distance from mesh network communication interface 307 and Wi-Fi assembly 315. These three components may be arranged in approximately a triangle to increase the distance between the components and decrease interference. For instance, in device 300, a distance of at least 74 mm between Wi-Fi assembly 315 and radar assembly 310 may be maintained. A distance of at least 98 mm between mesh network communication interface 307 and radar assembly 310 may be maintained. Additionally, distance between radar assembly 310 and speaker 318 may be desired to minimize the effect of vibrations on radar assembly 310 that may be generated by speaker 318. For instance, for device 300, a distance of at least 79 mm between radar assembly 310 and speaker 318 may be maintained. Additionally, distance between the microphones and radar assembly 310 may be desired to minimize any possible interference from the microphones on received radar signals. Top daughterboard 308 may include multiple microphones. For instance, at least 12 mm may be maintained between a closest microphone of top daughterboard 308 and radar assembly 310.

Other components may also be present. A third microphone assembly may be present, microphone assembly 311, which may be rear-facing. Microphone assembly 311 may function in concert with the microphones of top daughterboard 308 to isolate spoken commands from background noise. Power board 316 may convert power received from an AC power source to DC to power the components of device 300. Power board 316 may be mounted within device 300 using power bracket assembly 317. Rocker switch bracket 312, rocker switch board 313, and rocker switch button 314 may be collectively used to receive user input, such as up/down input. Such input may be used, for example, to adjust a volume of sound output through speaker 318. As another user input, button assembly 309 may include a toggle button that a user can actuate. Such a user input may be used to activate and deactivate all microphones, such as for when the user desires privacy and/or does not want device 300 to respond to voice commands.

Figure 4:
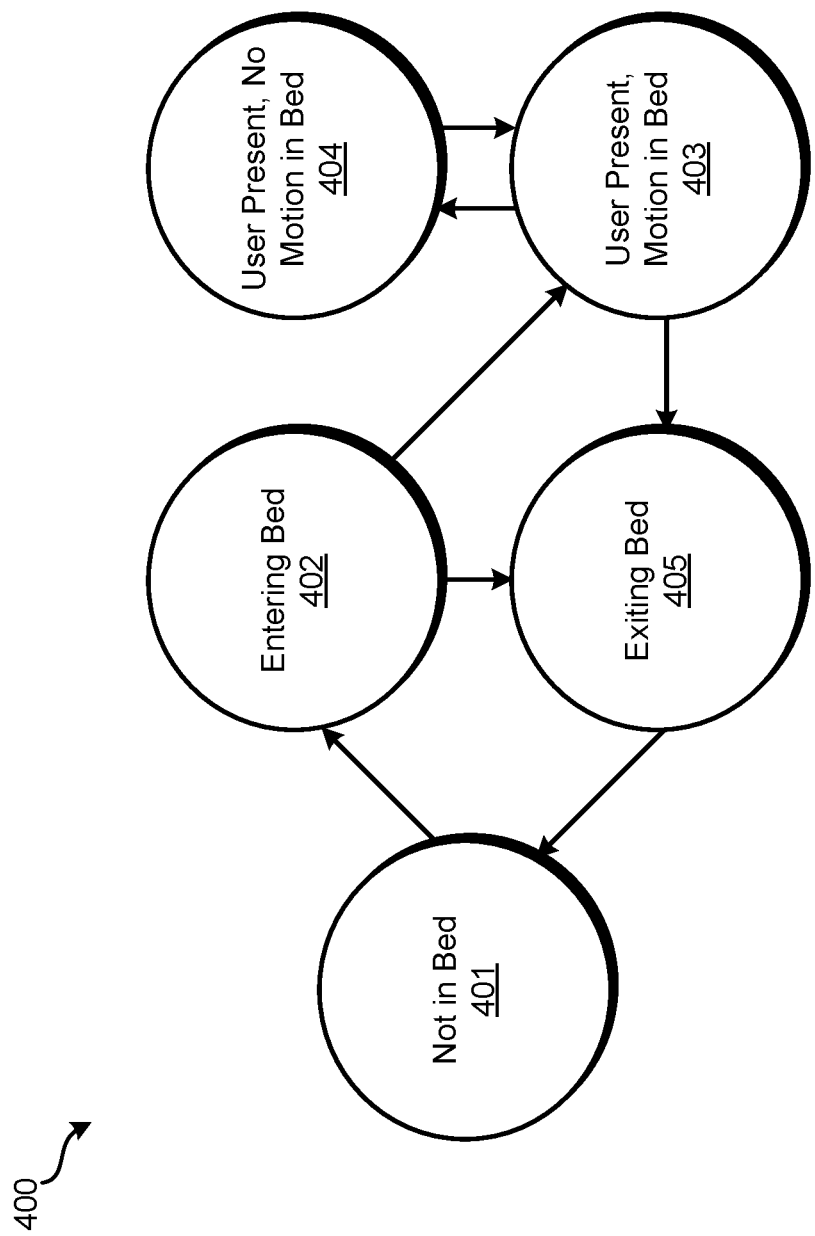
FIG. 4 illustrates an embodiment of a state system for determining when a person is sleeping.

FIG. 4 illustrates an embodiment of a state machine 400 for determining when a person is sleeping. Based upon data output by radar processing module 112, sleep state detection engine 114 may determine whether a person is sleeping using state machine 400. It should be understood that in some embodiments, sleep state detection engine 114 is incorporated as part of the functionality of radar processing module 112 and does not exist as a separate module. State machine 400 may include five possible sleep states: entering bed state 401; not in bed state 402; motion in bed state 403; no motion in bed state 405; and exiting bed state 404.

If no motion-indicative waveform data is present, this may be indicative that the user is not in bed. A user who is in bed can be expected to always be moving in at least small amounts due to their vital signs. Therefore, if zero movement is observed, the user may be judged to be in state 401. Following state 401 being determined, the next possible state that may be determined is state 402. In state 402, the monitored user is entering bed. Significant user motion may be sensed, such as according to Table 2. This may be indicative of a user entering bed and may cause the state to transition from state 401 to state 402.

From state 402, motion may continue to be detected in bed, such as due to the user rolling around, getting positioned, moving pillows, sheets, and/or blankets, reading a book, etc. State 402 may transition to state 403 while such motion continues to be detected. Alternatively, if motion is detected, then zero motion is detected, this may be indicative that state 405 has been entered by the monitored user exiting bed. If this condition occurs, state 402 may transition to state 405, then back to state 401. Generally, state 404 may be interpreted as the user being asleep and state 403 may be interpreted as the user being awake. In some embodiments, more than a threshold amount of time (or some other form of determination that uses a form of threshold criterion at least partially based on time) in state 404 is necessary to classify the user as asleep and more than a threshold amount of time (or some other form of determination that uses a form of threshold criterion at least partially based on time) in state 403 is necessary to classify the user as awake. For instance, movement in bed of less than five seconds may be interpreted as the user moving while still asleep if the user was previously determined to be asleep. Therefore, if a user transitions to state 403 from state 404, experiences some number of movement events, then returns to state 404 within less than a duration of time, the user may be identified as having experienced a "sleep arousal" in which the user's sleep is disturbed, but the user has not been awoken. Such sleep arousals may be tracked together with or separate data may be maintained from episodes where the user is judged to have fully awoken.

From state 403, the monitored user may be determined to be exiting bed at state 405 and may become motionless at state 404. To be "motionless" at state 404 refers to no large movements being performed by the monitored user, but the user continuing to perform small motions due to vital signs. In some embodiments, only when the monitored user's state is determined to be state 404 are vital signs treated as accurate and/or stored, recorded, or otherwise used to measure the user's vital signs. Data collected during state 403 and state 404 may be used to determine the monitored user's general sleep patterns (e.g., how much time tossing and turning, how much quality sleep, when deep sleep occurred, when REM sleep occurred, etc.). After a user enters state 404 for a predefined period of time, the user may be assumed to be asleep until the user exits state 404. When a user initially transitions to state 404, the user may be required to stay in state 404 for some amount of time, such as two to five minutes, to be considered asleep. If a user is in state 403 for at least a defined period of time, the user may be identified as awake. However, if the user enters state 403 from state 404 for less than the defined period of time, and returns to state 404, the user may be identified as just moving within their sleep and has been continuously asleep.

Figure 5:
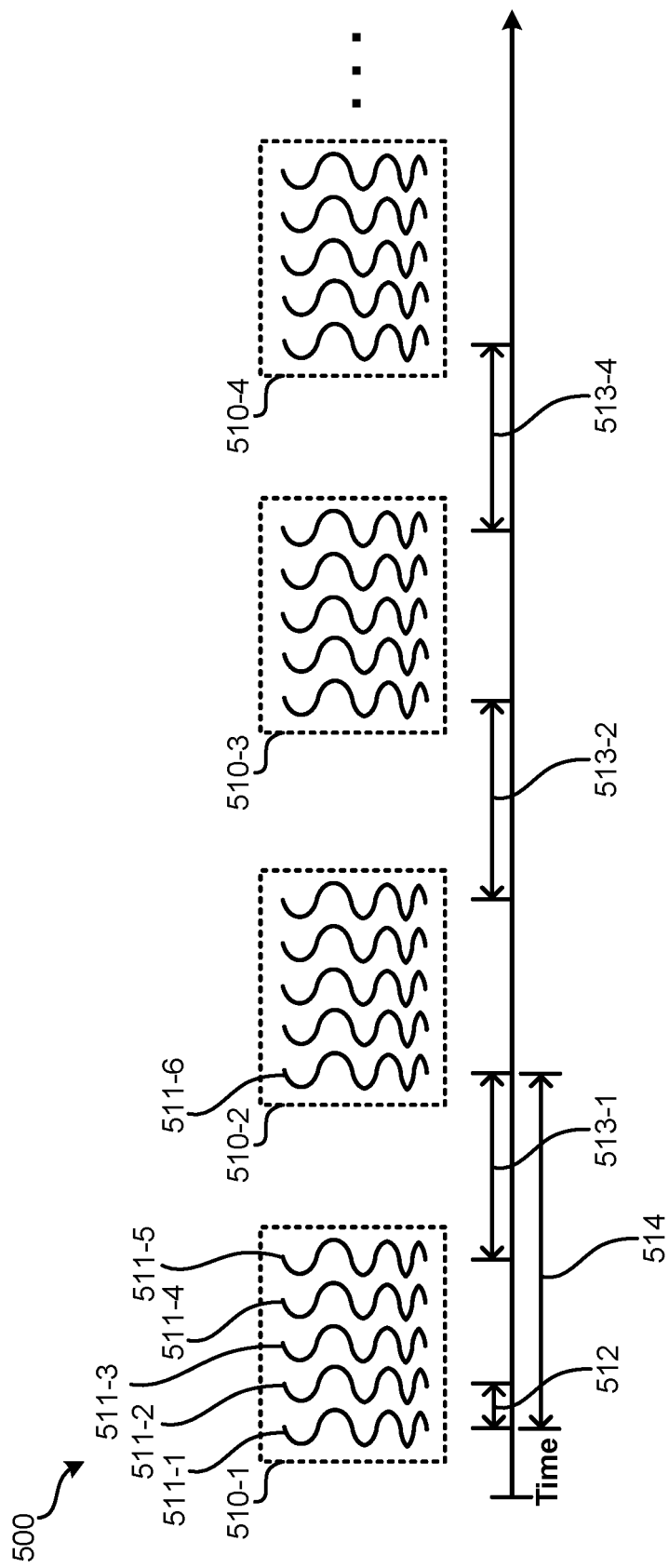
FIG. 5 illustrates a diagram of radar chirps being received in a burst mode.

FIG. 5 illustrates a diagram 500 of reflected radar chirps being received that were transmitted in a burst mode. Diagram 500 is representative of reflected, received radar chirps when radar subsystem 205 (or, more generally, radar subsystem 120) is operating in burst mode. In burst mode, bursts 510 (which can also be referred to as frames) are received by radar subsystem 205. A single burst includes some number of chirps. A reflected chirp is received for each chirp emitted by radar subsystem 205. As illustrated, burst 510-1 can include five reflected chirps: chirp 511-1, chirp 511-2, chirp 511-3, chirp 511-4, and chirp 511-5. In other embodiments, a burst includes greater or fewer numbers of chirps. For example, in some embodiments, a burst includes 3, 4, 10, 15, 20, or some other number of chirps. A burst may include any number of chirps between 2 and 100 chirps.

Within a burst, such as burst 510-1, chirps may be transmitted, and thus reflected and received, about every 0.333 ms. Therefore, time 512 may be 0.333 ms. In other embodiments, time 512 is greater or smaller. For instance, time 512 may be between 0.01 ms and 5 ms. The burst period, that is, time 514, which represents the amount of time between burst 510-1 beginning and burst 510-2 beginning may be 33.3 ms. In other embodiments, time 514 is larger or smaller, such as between 15 ms and 500 ms. Between each burst, such as between burst 510-1 and burst 510-2 a relatively larger amount of time can elapse than between adjacent chirps within a burst. For example, the amount of time, time 513-1, between burst 510-1 and burst 510-2 (that is, the amount of time elapsing between chirp 511-5 and chirp 511-6 may be 26.7 ms. In other embodiments, time 513-1 is greater or smaller, such as any value between 1 ms and 200 ms. Regardless of the embodiment, time 513-1 larger than time 512; that is, the time between adjacent chirps within a burst or frame is smaller than the time between bursts.

The timing between bursts 513 may be fixed; therefore, time 513-1, time 513-2, and time 513-4 may be the same. Similarly, the time between chirps within a burst can be constant. The radar subsystem can continuously operate in this mode without needing to change mode for vital detection.

Figure 6:
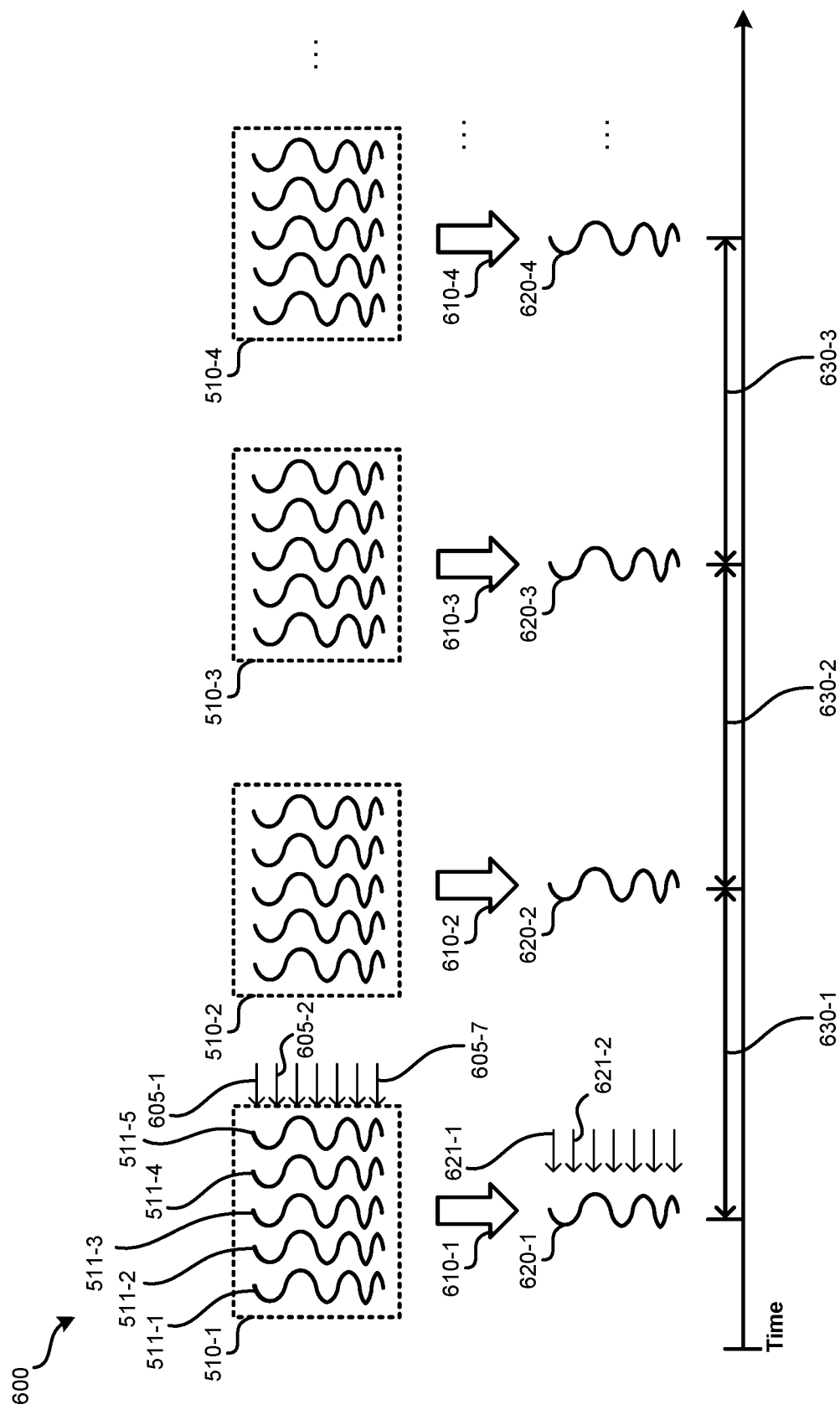
FIG. 6 illustrates a diagram of radar chirps being received in a burst mode and converted to a virtual continuous mode.

FIG. 6 illustrates a diagram 600 of radar chirps being received as part of a burst mode radar data stream and converted to a virtual continuous mode radar data stream. As a reflected radar chirp is received by the radar subsystem, it may be mixed with the frequency currently being emitted, thus creating a mixed received radar chirp. The conversion of diagram 600 may be performed by virtual continuous chirp creator 240 based on the raw chirp waterfall output by the radar subsystem. As detailed in relation to FIG. 5, the radar sensor may operate in burst mode and, thus, may receive reflected radar chirps in a burst pattern. The waveform data or raw chirp waterfall output by the radar subsystem operating in burst mode can be referred to as a burst mode radar data stream. This burst mode radar data stream is indicated in FIG. 6 by the graphical representations of bursts 510 and chirps 511.

Conversions 610 are performed to convert each reflected burst in the raw chirp waterfall to a single, representative virtual continuous radar chirp 620. Conversion 610-1 (represented by an arrow) converts reflected burst 510-1 to virtual continuous radar chirp 620-1; conversion 610-2 converts burst 510-2 to virtual continuous chirp 620-2; conversion 610-1 converts burst 510-3 to virtual continuous chirp 620-3; conversion 610-4 converts burst 510-4 to virtual continuous chirp 620-4, and so on.

To perform conversion 610-1, each of chirps 511-1 through 511-5, is sampled a number of times from the burst mode radar data stream. This sampling can occur at some number of chirp sampling points, such as chirp sampling point 605-1 though chirp sampling point 605-7. (The arrows representing sampling points 605-3, 605-4, 605-5, and 605-6 are not labelled for simplicity of FIG. 6.) As an example, if five chirps are present in burst 510-1 and seven chirp sampling points are used, a total of 35 samples (7 samples for each chirp) may be sampled from burst 510-1. The number of chirp sampling points used may vary by embodiment and may be greater or fewer than the seven chirp sampling points shown in FIG. 6.

As part of conversion 610-1, an averaging or combining process may be performed. Generally, each of the chirps of burst 510-1 (chirp 511-1 through chirp 511-5) may be averaged together. To accomplish this averaging: the sample for each chirp of burst 510-1 taken at chirp sampling point 605-1 may be averaged together; the sample for each chirp of burst 510-1 taken at chirp sampling point 605-2 may be averaged together; the sample for each chirp of burst 510-1 taken at chirp sampling point 605-3 may be averaged together; the sample for each chirp of burst 510-1 taken at chirp sampling point 605-4 may be averaged together; the sample for each chirp of burst 510-1 taken at chirp sampling point 605-5 may be averaged together; the sample for each chirp of burst 510-1 taken at chirp sampling point 605-6 may be averaged together; and the sample for each chirp of burst 510-1 taken at chirp sampling point 605-7 may be averaged together. Stated more generally, each sample of a chirp is averaged with a corresponding sample of each other chirp of the burst. For example, the third sample of a chirp is averaged with the third samples of each other chirp of the burst.

For the illustrated embodiment, the seven averaged samples may then be used to construct a virtual continuous radar chirp 620-1. For instance, the first averaged value from chirp sampling point 605-1 is used as the first sample 621-1 of virtual continuous radar chirp 620-1; the second averaged value from chirp sampling point 605-2 is used as the second sample 621-2 of virtual continuous radar chirp 620-1, and so on. Stated more generally, the averaged samples of burst 510-1 are concatenated to create virtual continuous radar chirp 620-1.

Stated another way, sample-wise averaging is performed for each of burst 510. Mathematically, each chirp in a burst can be represented using the notation $c_{i,j}$, where i is the index for the sample of the chirp and j is the index for the chirp within the burst. Therefore, $c_{2,3}$ would be the second sample of the third chirp within a given burst. Equation 4 can be used to find the average values used to create the virtual continuous radar chirp:

$$V_k = \text{average } (c_{k,1}, c_{k,2}, c_{k,3}, c_{k,N}) \qquad \text{Eq. 4}$$

In Equation 4, N represents the number of chirps within the burst and k represents the sample number. $V_k$ represents the averaged value corresponding to the kth sample. Equation 4 would be repeated k times to obtain all $V_k$ values that are used to construct the virtual continuous radar chirp.

The created virtual continuous radar chirps 620 may be spaced in time at equal intervals. For instance, time 630-1 may be 33.3 ms, which may match the burst period detailed in relation to FIG. 5. Times 630-2, 630-3, etc., can match time 630-1 such that the virtual continuous radar chirps are output periodically. More generally, since a single virtual continuous radar chirp is generated for each burst of bursts 510, times 630 may be the same as the period of bursts 510. By each virtual continuous radar chirp being equally spaced in time, the virtual continuous radar chirps may be more effective than the burst mode radar data stream to use for health monitoring. Virtual continuous radar chirps 620 may be output as a virtual continuous mode radar data stream to other components for processing. If such other components are implemented as software, the processing may be performed using the same processor(s) or processing system used to perform the functions of virtual continuous chirp creator 240.

By chirps 511 of burst 510-1 being averaged together, virtual continuous radar chirp 620-1 can be higher resolution than any of individual chirps 511. The reflected radar received by radar subsystem 120 (or 205) may be converted to digital data using an analog to digital converter (ADC). The ADC may have a limited resolution, such as 8 bits. Therefore, all the values output by the ADC may be limited to a range of 0 to 256, which corresponds to eight binary bits. Dithering is a concept in signal processing that can result in trading signal fidelity for an increase in resolution. By averaging or otherwise combining multiple reflected noisy chirps, dithering can be exploited to obtain a resolution higher than output by the ADC used to convert the analog radar signals to the digital waveform data present in the digital burst mode radar data stream. The intuition is that a sample in a series of noisy chirps will dither around the true value slightly with added ADC noise. With multiple chirps being aggregated, measured values are captured in a statistically accurate way. Without noise, even with many chirps in burst, there can be no statistical advantage as each sample over the chirps will have the same value that can suffer from ADC quantization. The resulting higher-resolution signal with dithering has a higher fidelity in detecting weak signatures, such as human vital signs (e.g. breathing, heartbeats).

Figure 7:
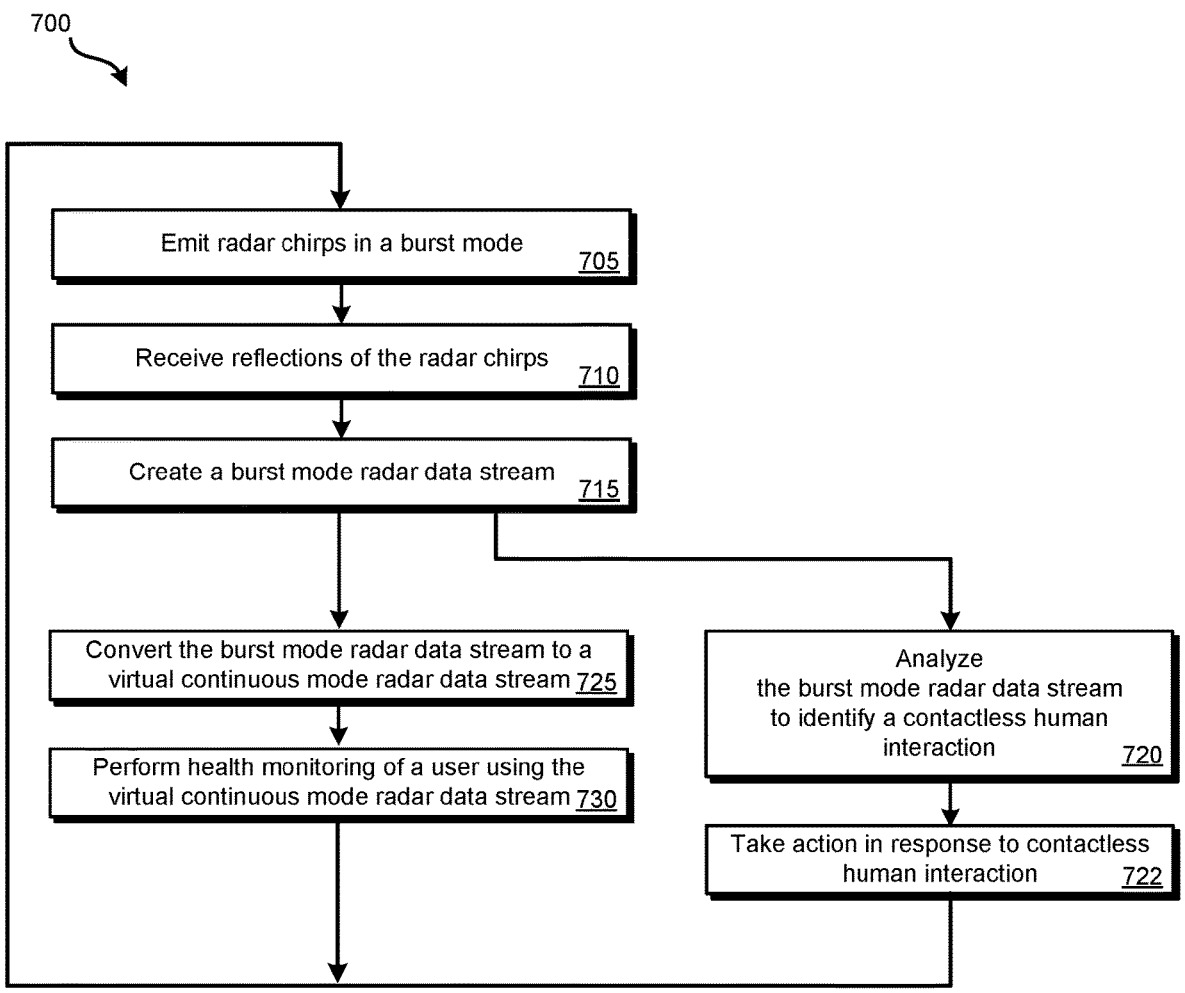
FIG. 7 illustrates an embodiment of a method for monitoring for contactless human interactions and monitoring health using a single radar modulation mode.

Various methods may be performed using the systems and arrangements detailed in relation to FIGS. 1-6. FIG. 7 illustrates an embodiment of a method 700 for monitoring for contactless human interactions and monitoring health using a single radar modulation mode. Method 700 can be performed using the devices and systems detailed in relation to FIGS. 1-3B.

At block 705, radio waves are emitted by a radar subsystem or radar sensor. The radio waves emitted may be continuous-wave radar, such as FMCW, as detailed in relation to FIG. 2C. The radar sensor may operate in burst mode, such that radar chirps are emitted (and therefore received) in a pattern similar to FIG. 2C. The radio waves emitted may be emitted by RF emitter 206 of radar subsystem 205, which may use one or more antennas to emit the radio waves. At block 710, reflections of the radio waves may be received, such as by RF receiver 207 of radar subsystem 205. The reflections received at block 810 may be reflected off of moving objects (e.g., a person having a heartbeat and breathing) and stationary objects. The pattern of received, reflected radio waves may approximately mirror the pattern in which the radio waves were emitted; therefore, diagram 500 may approximately represent the pattern in which the bursts of chirps were transmitted and also bursts of reflected chirps were received.

At block 715, a raw chirp waterfall, which can be referred to as a burst mode radar data stream, is created based on received reflected radio waves. The radar subsystem or sensor may use an on-board ADC to convert the received, reflected radar signals to the digital domain. In some embodiments, data received from different antennas of the radar subsystem is maintained separately. The digital burst mode radar data stream may be output by the radar subsystem to a processing system, such as a processing system that performs the functions of virtual continuous chirp creator 240 and/or human interaction engine 245.

At block 720 the burst mode radar data stream may be analyzed to determine if any contactless human interaction is present, such as a gesture or a human presence. The burst mode radar data stream may be analyzed directly for this human interaction regardless of the state of health monitoring performed in blocks 725 and 730. If a contactless human interaction is detected at block 720, one or more actions may be taken at block 722 in response to the detection. For instance, a command may be executed or output to another device based on the detected gesture. If a human presence is detected, an action may be taken, such as illuminating electronic display 140 (and presenting information) or outputting audio, such as synthesized speech.

Independent of blocks 720 and 722, method 700 can involve block 725 being performed. Therefore, block 725 may be performed while blocks 720 and/or 720 are being performed. At block 725, the same burst mode radar data stream that was, is, or will be analyzed for a contactless human interaction at block 720 can be processed to create a virtual continuous chirp radar data stream. As detailed in relation to FIG. 6, a conversion, which can involve an averaging process, may be performed to convert a burst of radar chirps to a virtual continuous radar chirp. Multiple virtual continuous chirps are assembled into a virtual continuous radar data stream that is output (as digital data) to one or more other components, which may be implemented using the same processing system that created the virtual continuous radar data stream or a separate processing system. By combining multiple chirps within a burst into a single virtual continuous mode chirp, the virtual continuous mode chirp can benefit from dithering, and thus have a higher resolution than individual chirps of a burst present in the burst mode radar data stream.

At block 730, health monitoring, such as sleep tracking, vital sign monitoring, cough monitoring, or sleep disturbance attribution may be performed as detailed in relation to the functionality of radar processing module 210. The health monitoring may function or may function more effectively based on a continuous radar data stream as opposed to a burst mode radar data stream. In other embodiments, some other form of monitoring or tracking can be performed based on the continuous radar data stream.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A contactless health monitoring device, comprising:
a housing;
a radar sensor, housed by the housing, configured to operate in a burst mode in which the radar sensor emits a plurality of bursts of radar chirps, wherein:
a first amount of time elapsing between adjacent radar chirps of a burst of the plurality of bursts of radar chirps is smaller than a second amount of time elapsing between adjacent bursts of the plurality of bursts of radar chirps; and
the radar sensor outputs a burst mode radar data stream that is based on received reflections of the radar chirps of the plurality of bursts of radar chirps;
a processing system, housed by the housing, comprising one or more processors, that is in communication with the radar sensor, the processing system configured to:
receive the burst mode radar data stream from the radar sensor;
analyze the burst mode radar data stream to identify a contactless human interaction;
convert the burst mode radar data stream to a virtual continuous mode radar data stream; and
perform health monitoring of a user using the virtual continuous mode radar data stream.

2. The contactless health monitoring device of claim 1, wherein the virtual continuous mode radar data stream comprises a plurality of virtual reflections of radar chirps spaced equally in time.

3. The contactless health monitoring device of claim 2, wherein the processing system being configured to convert the burst mode radar data stream to the virtual continuous mode radar data stream comprises the processing system being configured to:
create a virtual reflection of a radar chirp based on the multiple radar chirps of a burst of the plurality of bursts, wherein the virtual reflection of the radar chirp is part of the plurality of virtual reflections of radar chirps spaced equally in time.

4. The contactless health monitoring device of claim 3, wherein the processing system being configured to create the virtual reflection of the radar chirp based on the multiple radar chirps of the burst of the plurality of bursts comprises the processing system being configured to perform an averaging process, comprising:
sampling a plurality of samples of each radar chirp of the multiple chirps of the burst;
averaging each sample of the plurality of samples with corresponding samples from the other chirps of the multiple chirps of the burst to create a plurality of averaged samples; and
assembling the averaged samples to create the virtual reflection of the radar chirp.

5. The contactless health monitoring device of claim 4, wherein the contactless human interaction is detected while health monitoring is being performed.

6. The contactless health monitoring device of claim 1, wherein the radar sensor outputs frequency-modulated continuous wave (FMCW) radar having a frequency between 57-64 GHz and a peak EIRP of less than 20 dBm.

7. The contactless health monitoring device of claim 1, wherein the contactless human interaction is a gesture.

8. The contactless health monitoring device of claim 1, wherein the contactless human interaction is presence detection.

9. The contactless health monitoring device of claim 1, wherein the health monitoring comprises sleep monitoring of the user.

10. The contactless health monitoring device of claim 1, wherein the virtual continuous mode radar data stream has higher resolution than the burst mode radar data stream due to dithering.

11. The contactless health monitoring device of claim 1, further comprising:
a wireless network interface housed by the housing;
an electronic display housed by the housing;
a microphone housed by the housing; and
a speaker housed by the housing, wherein the wireless network interface, the electronic display, the microphone, and the speaker are in communication with the processing system.

12. The contactless health monitoring device of claim 11, wherein the processing system is further configured to:
receive a spoken command via the microphone;
transmit an indication of the spoken command via the wireless network interface to a cloud-based server system;
receive a response from the cloud-based server system via the wireless network interface; and
output information obtained from the performed health monitoring via the electronic display, the speaker, or both based on the response from the cloud-based server system.

13. The contactless health monitoring device of claim 1, wherein the processing system is further configured to output a report based on the health monitoring.

14. A method for monitoring for contactless human interactions and monitoring health using a single radar modulation mode, the method comprising:
emitting radar chirps, by a radar sensor operating in a burst mode, such that the radar sensor emits a plurality of bursts of radar chirps, wherein:
a first amount of time elapsing between subsequent radar chirps of a burst of the plurality of bursts of radar chirps is smaller than a second amount of time elapsing between subsequent bursts of the plurality of bursts of radar chirps; and
the radar sensor outputs a burst mode radar data stream that is based on reflections of the radar chirps of the plurality of bursts or radar chirps;
receiving, by a processing system, the burst mode radar data stream from the radar sensor;
analyzing, by the processing system, the burst mode radar data stream for a contactless human interaction;
converting, by the processing system, the burst mode radar data stream to a virtual continuous mode radar data stream; and
performing, by the processing system, health monitoring of a user using the virtual continuous mode radar data stream.

15. The method for monitoring for contactless human interactions and monitoring health using the single radar modulation mode of claim 14, wherein the virtual continuous mode radar data stream is comprised of a plurality of virtual reflections of radar chirps spaced equally in time.

16. The method for monitoring for contactless human interactions and monitoring health using the single radar modulation mode of claim 15, wherein converting the burst mode radar data stream to the virtual continuous mode radar data stream comprises:
creating a virtual reflection of a radar chirp based on the multiple radar chirps of a burst of the plurality of bursts, wherein the virtual reflection of the radar chirp is part of the plurality of virtual reflections of radar chirps spaced equally in time.

17. The method for monitoring for contactless human interactions and monitoring health using the single radar modulation mode of claim 16, wherein creating the virtual reflection of the radar chirp based on the multiple radar chirps of the burst of the plurality of bursts comprises:
   sampling a plurality of samples of each radar chirp of the multiple chirps of the burst;
   averaging each sample of the plurality of samples with corresponding samples from the other chirps of the multiple chirps of the burst to create a plurality of averaged samples; and
   assembling the averaged samples to create the virtual reflection of the radar chirp.

18. The method for monitoring for contactless human interactions and monitoring health using the single radar modulation mode of claim 17, wherein the contactless human interaction is a gesture.

19. The method for monitoring for contactless human interactions and monitoring health using the single radar modulation mode of claim 17, wherein the contactless human interaction is presence detection.

20. The method for monitoring for contactless human interactions and monitoring health using the single radar modulation mode of claim 17, wherein the health monitoring comprises sleep monitoring of the user.

\* \* \* \* \*